US007678558B2

(12) United States Patent
Comstock et al.

(10) Patent No.: US 7,678,558 B2
(45) Date of Patent: *Mar. 16, 2010

(54) METHOD FOR OVEREXPRESSION OF ZWITTERIONIC POLYSACCHARIDES

(75) Inventors: Laurie E. Comstock, Medfield, MA (US); Katja G. Weinacht, Denzlingen (DE); Michael J. Coyne, North Attleboro, MA (US); Dennis L. Kasper, Charlestown, MA (US); Arthur O. Tzianabos, Reading, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/654,246

(22) Filed: Jan. 17, 2007

(65) Prior Publication Data

US 2007/0154991 A1    Jul. 5, 2007

Related U.S. Application Data

(63) Continuation of application No. 10/388,390, filed on Mar. 13, 2003, now Pat. No. 7,166,455.

(60) Provisional application No. 60/364,168, filed on Mar. 13, 2002.

(51) Int. Cl.
*C12N 1/12* (2006.01)
*C12P 21/06* (2006.01)
*C12P 19/34* (2006.01)
*C12P 19/04* (2006.01)
*C12N 1/20* (2006.01)
*A01N 63/00* (2006.01)
*C07H 21/04* (2006.01)

(52) U.S. Cl. ............... 435/252.1; 435/252.3; 435/69.1; 435/91.1; 435/101; 435/183; 435/221; 435/252.5; 435/320.1; 435/471; 435/476; 435/477; 435/490; 424/93.46; 424/93.2; 424/93.1; 436/23.2

(58) Field of Classification Search ................. None
See application file for complete search history.

(56) References Cited

U.S. PATENT DOCUMENTS

| 4,740,480 | A | 4/1988 | Ooka |
| 4,952,524 | A | 8/1990 | Lee et al. |
| 5,229,315 | A | 7/1993 | Jun et al. |
| 5,468,676 | A | 11/1995 | Madan |
| 5,576,241 | A | 11/1996 | Sakai |
| 5,679,654 | A | 10/1997 | Tzianabos et al. |
| 5,700,787 | A | 12/1997 | Tzianabos et al. |
| 5,851,808 | A | 12/1998 | Elledge et al. |
| 5,853,718 | A | 12/1998 | Molin et al. |
| 5,868,870 | A | 2/1999 | Fazan et al. |
| 7,026,285 | B2 | 4/2006 | Tzianabos et al. |
| 7,083,777 | B1 | 8/2006 | Tzianabos et al. |
| 7,166,455 | B2 * | 1/2007 | Comstock et al. ........ 435/252.1 |
| 2004/0092433 | A1 | 5/2004 | Wang et al. |
| 2004/0219160 | A1 | 11/2004 | Tzianabos et al. |
| 2006/0153832 | A1 | 7/2006 | Tzianabos et al. |
| 2007/0020730 | A1 * | 1/2007 | Comstock et al. ........ 435/69.1 |
| 2008/0057565 | A1 | 3/2008 | Comstock et al. |

FOREIGN PATENT DOCUMENTS

| WO | WO 96/07427 A1 | 3/1996 |
| WO | WO 02/07741 A1 | 1/2002 |
| WO | WO 02/45708 A2 | 6/2002 |

OTHER PUBLICATIONS

Dias et al., Antisense oligonucleotides: Basic concepts and mechanisms. Mol. Cancer Therap., 2002, vol. 1: 347-355.*
Bayley DP et al. Analysis of cepA and other *Bacteroides fragilis* genes reveals a unique promoter structure. (2000) *FEMS Microbiol Lett* 193:149-54.
Comstock Le et al. Analysis of a capsular polysaccharide biosynthesis locus of *Bacteroides fragilis*. (1999) *Infect Immun* 67:3525-32.
Coyne M et al. Polysaccharide biosynthesis locus required for virulence of *Bacteroides fragilis*. (2001) *Infect Immun* 69:4342-50.
Coyne MJ et al. *Bacteroides fragilis* NCTC9343 produces at least three distinct capsular polysaccharides: cloning, characterization, and reassignment of polysaccharide B and C *Biosynthesis loci*. (2000) *Infect Immun* 68:6176-81.
Gally DL et al. Environmental regulation of the *fim* switch controlling type 1 fimbrial phase variation in *Escherichia coli* K-12: effects of temperature and media. (1993) *J Bacteriol* 175:6186-93.
Krinos CM et al. Extensive surface diversity of a commensal microorganism by multiple DNA inversions. (2001) *Nature* 414:555-8.
Lysnyansky I et al. Juxtaposition of an active promoter to vsp genes via site-specific DNA inversions generates antigenic variation in *Mycoplasma bovis*. (2001) *J Bacteriol* 183:5698-5708.
McClain MS et al. Inversion-independent phase variation of type 1 fimbriae in *Escherichia coli*. (1993) *J Bacteriol* 175(14):4335-44.
Pantosti A et al. Immunochemical characterization of two surface polysaccharides of *Bacteroides fragilis*. (1991) *Infect Immun* 59:2075-82.
Schembri MA et al. Orientation-dependent enhancement by H-NS of the activity of the type 1 fimbrial phase switch promoter in *Escherichia coli*. (1998) *Mol Gen Genet* 259:336-44.
Smith SG et al. Functional analysis of the FimE integrase of *Escherichia coli* K-12: isolation of mutant derivatives with altered DNA inversion preferences. (1999) *Mol Microbiol* 34:965-79.

(Continued)

*Primary Examiner*—Ganapathirama Raghu
(74) *Attorney, Agent, or Firm*—Wolf, Greenfield & Sacks, P.C.

(57) ABSTRACT

The present invention is directed to methods for producing and selecting novel mutant strains of *B. fragilis* that constitutively express a particular capsular polysaccharide or only selected capsular polysaccharides; compositions directed to the novel mutant strains of *B. fragilis* that constitutively express a particular capsular polysaccharide or only selected capsular polysaccharides; improved methods for purification of individual capsular polysaccharides; and compositions directed to novel res02 and inv19 genes and their gene products. Significantly, the present invention provides methods and compositions for overexpressing and purifying immunomodulatory capsular polysaccharide A (PSA) in high yield.

6 Claims, 5 Drawing Sheets

OTHER PUBLICATIONS

Tzianabos A et al. The capsular polysaccharide of *Bacteroides fragilis* comprises two ionically linked polysaccharides. (1992) *J Biol Chem* 267:18230-18235.

Tzianabos AO et al. T cells activated by zwitterionic molecules prevent abscesses induced by pathogenic bacteria. (2000) *J Biol Chem* 275:6733-40.

Weinacht K et al. Phase variation of the capsular polysaccharides of *Bacteroides fragilis* is dictated by site-specific recombinases. *2002 General Meeting of the American Society for Microbiology*, May 19-23, 2002. Abstract.

Zhao H et al. In vivo phase variation of MR/P fimbrial gene expression in *Proteus mirabilis* infecting the urinary tract. (1997) *Mol Microbiol* 23:1009-19.

Chen J et al., DNA inversion on conjugative plasmid pVT745. J Bacteriol. Nov. 2002;184(21):5926-34.

Coyne MJ et al., Mpi recombinase globally modulates the surface architecture of a human commensal bacterium. Proc Natl Acad Sci U S A. Sep. 2, 2003;100(18):10446-51. Epub Aug. 12, 2003.

Xu J et al., A genomic view of the human-*Bacteroides thetaiotaomicron* symbiosis. Science. Mar. 28, 2003;299(5615):2074-6.

Brubaker et al., Mitogenic Activity of Purified Capsular Polysaccharide A from *Bacteroides fragilis*: Differential Stimulatory Effect on Mouse and Rat Lymphocytes In Vitro, *J. Immunol.* 162:2235-2242 (1999).

Pantosti et al., *Bacteroides fragilis* Strains Express Multiple Capsular Polysaccharides, *J. Clin. Microbiol.* 31(7):1850-1855 (1993).

Tzianabos A.O., Polysaccharide Immunomodulators as Therapeutic Agents: Structural Aspects and Biologic Function, *Clin. Microbiol. Rev.* 13(4):523-533 (2000).

Grabow, Bacteriophages: Update on application as models for viruses in water. Water SA 2001;27(2):251-268.

Salyers et al., Conjugative transposons: an unusual and diverse set of integrated gene transfer elements. Microbiol Rev. Dec. 1995;59(4):579-90. Review.

Ward et al., The nucleotide sequence of the *tnp*A gene of Tn21, *Nucleic Acids Research*, vol. 15(4), 1987, 1799-1806.

Blomfield et al. Lrp stimulates phase variation of type 1 fimbriation in *E. coli* K12. *J. Bacteriology* 175, 27-36, 1993.

Eisenstein et al. Integration host factor is required for the DNA inversion that controls phase variation in *E. coli*. Proc Natl. Acad. Sci. 84, 6506-6510, 1987.

Grabow. Bacteriophages: Update on application as models for viruses in water. Water SA 2001; 27(2): 251-268.

Harth et al. Treatment of mycobacterium tuberculosis with antisense oligonucleotides to glutamine synthetase mRNA inhibits glutamine synthetase activity, formation of poly-L-glutamate/glutamine cell wall structure, and bacterial replication. *Proc. Natl. Acad. Sci.* 97: 418-423, 2000.

Kernodle et al. Expression of an antisense *hla* fragment in *Staphylococcus aureus* reduces alpha-toxin production in vitro and attenuates lethal activity in a murine model. *Infection and Immunity* 179-184. 1997.

Salyers et al., Conjugative transposons: an unususal and diverse set of integrated gene transfer elements. Microbiol Rev. 1995 59: 79-90.

\* cited by examiner

Figure 1
SEQ ID NO:1

```
atggtaatagcttatttgagagtaagtacggaaaaacagttttttggctaatcagaaggaa    60
gagattatgcgatttgcagagaagaatgggttgtcgattgacaagtggtacacagagacc    120
gtaagcggaagcgtgagcacaaaagacagaaagctatcagagttattgaagagaatgcat    180
cccggggatacactgattgtaacggagatttcgagattgagccgtacactgctcgagatt    240
atgactatcctgaattttgtattaagaagcaggtagtgctctatagcaccaaagagggc    300
tatgtgtttcaggacgacatcaacagcaaggtgctgggattcgcgttcggactgatggcg    360
gaaatagaaaggaacctgatttcgatgcgtaccaaagaagctctcgcacgcagaaagcag    420
gaaggaatgactttaggccgaagaaaggggatacgcctaaaataaaattgctgcgtgcc    480
aataagcgcgtacttaccaaagaacttgacaaaggaactacttactcggaattggcggag    540
aagatgggggtatccagaacaaccctgttccggtttatgaaaacgatgtattag         594
```

Figure 2
SEQ ID NO:2

```
MVIAYLRVSTEKQFLANQKEEIMRFAEKNGLSIDKWYTETVSGSVSTKDRKLSELLKRMH    60
PGDTLIVTEISRLSRTLLEIMTILNFCIKKQVVLYSTKEGYVFQDDINSKVLGFAFGLMA   120
EIERNLISMRTKEALARRKQEGMTLGRKKGDTPKIKLLRANKRVLTKELDKGTTYSELAE   180
KMGVSRTTLFRFMKTMY                                              197
```

Figure 3
SEQ ID NO:3

```
atggaaatagaaaaattcattaaatctttagcaagaaaagcgaagttaggcgggcgttac    60
agcacagccaatacctacctctacactttgcacagttttcagaagtttgcgggaaaagcc   120
tcactgacttttgaagagatcactcccgagagtatcaaggagtacgagcaatacttaatc   180
ctcaacgggaaacggtacaacacgatctcgctctacatgcgcatgttgcgttccatctgc   240
aatcaggcatcggagcagaacatagcttcgctcaacacccgcgagctgtttgagaatgtt   300
tttatcggcaacgaacccactgccaagcgtgccatctcacccgtcctcatttcccgcctg   360
ctcgaagcagatttcagcaagaacagccggctcgattttgcccgcgacctcttcttgcta   420
agcttctacctgaggggaatcccgtttgtcgacctggtacatctccgcaagaccgatgtg   480
cagggaaacatgctcgtttatttccgccagaaaacgggacagcaacttacggtaatcata   540
gaaaactgcgccaaagtgatcttgcgtaagtatgcctcgctttgcaaagaatccgtctat   600
ctgctgcccgtcatcagcgcagccggagaggaggggcacaagcagtaccgaagtgcattg   660
agggtatacaacaaacgcctcaaccagatatccggaatactgaaattgaagactccgctg   720
acctcttatgtggcacgccacagttgggcgaccacggccctgcagaaggggttccggtt   780
tcagtgatcagtgcaggaatggggcatgcttcagagaaggtgacatacatttatctggca   840
tcttttgataacaaaacgctcagtaacgcaaataaaaaagtgattgccgccgtgagattt   900
aagaaagaggaggaggagtga                                          921
```

Figure 4
SEQ ID NO:4

```
MEIEKFIKSLARKAKLGGRYSTANTYLYTLHSFQKFAGKASLTFEEITPESIKEYEQYLI    60
LNGKRYNTISLYMRMLRSICNQASEQNIASLNTRELFENVFIGNEPTAKRAISPVLISRL   120
LEADFSKNSRLDFARDLFLLSFYLRGIPFVDLVHLRKTDVQGNMLVYFRQKTGQQLTVII   180
ENCAKVILRKYASLCKESVYLLPVISAAGEEGHKQYRSALRVYNKRLNQISGILKLKTPL   240
TSYVARHSWATTALQKGVPVSVISAGMGHASEKVTYIYLASFDNKTLSNANKKVIAAVRF   300
KKEEEE                                                         306
```

Figure 6
SEQ ID NO:5

```
agtactgataactccggtgactcccgccactgtaaaagaaaatgccggagaagctcccca      60
gggacaagacgtaaacgctacggtgaaaaatgacacggtgttcttcgacaaaattgccggt    120
aaccgaacttattacctccattgtaggcgataaagacaaagcggaagccattgtcaaagc    180
catcggtgacgtaaaatacaaagtaggctacaagccggctctcaacacagagaaggacag    240
catctaccttgctttcgatccgaaaccgttgacccttcaactgcctgcagccgtagaagg    300
ccaggaaggacagactgttaccgtaaccatttcgtctccggacaaaggcagctttgctta    360
caagaaaaatcagttgaagttgaagctcagcgccgataaagtggaactggcaggcgtagc    420
ggtacctgttcctcagaccctgttcgacttcggtatgaccaaaaagaagtgattgcctgt    480
tcaacacacgtaacaagcagtagtcataggggtaaagcctgtaaagacaggctttatac    540
ccgcatgaaaaagtccgtgctctccccccggagtgaacacggactttctgttccttgaa    600
accattcaaaaaaaaagattatttcacagcagccaatgccttttcataatccggctcct    660
gagtaatctccggcacaagctctgtataagctactttcccgtctttcccaatcaccacta    720
ccgcacgcgccagcagtccggccagcggtccgtcagccatcctcacgccatagctctcgt    780
cgaagtccgaaaagcggaaatccgacaacggaatcacgttttcgatacctctgtcgtgc    840
agaagcgtccctgcgcaaacggcaagtctttcgaaatggccaataccacggtatccttca    900
ttccggctgccatttattgaatttacgcaccgaagtggcgcacacaccggtatccagac    960
tcgggaaaatattcagaacaatattcttacctttcagatcttttagtgcgaaagaagata   1020
aatcacttttcaccagctcgaaatcgggagccacctttccaacctgtataaattcgccaa   1080
tcagctttaccggttgtcctttgaaatttgttgttgccataattgataactctaagtttt   1140
atttactatattctaaacaatcggtgcaagaactttgttcacgatggacaataatctaaa   1200
aaataaaattgatatgaaaactttattcgacgagatggaacacgcagtcaaaaactggtg   1260
gttatctcttattctgggtattctgtacatcatcgtggctctctgtctgctattcgcacc   1320
gggaagcagttacattgccctcagcgtcatcttcagcatttcgatgctgataagtggtat   1380
catcgaaatcatcttctccatcagtaaccggcgaggcatctcgtcctggggatggtacct   1440
cgcaggcggtatcatcgatctgatcttaggcatctacctggtagcctatccgctgctcag   1500
catggaagtcataccgttcatagtcgccttctggatgatgttccgcggtttctccgccac   1560
aggctattctatggacctgaagcgttatggcacccgtgagtggggatggtacatgggatt   1620
cggcatcctcgccatcatttgttcgctgatcatcctgtggcagccggccgtaggtgccct   1680
ctacgttatatatgctggcattcactttcctgatcatcggattcttccgtgtcatgtt   1740
gtccttcgaactgaaaagccttcataaacgatcaacggtgatgaacggtaaatgataaac   1800
attgaatgaacccctattcaccacagattacacagattaacacagatattttaattaaac   1860
tctcagtaaaataaattattaatctgtgagaatctgtgtaatctgcggtgaattatgact   1920
cccctaaccgttactaatacatcgttttcataaaccgg                          1958
```

Figure 7
SEQ ID NO:6

```
ttttccgtacttactctcaaataagctattaccataattcatgtttttaaatgattaata      60
caccacgaaaaaacggctattcattcaaatacgggacactttttttacgttcctttttttct    120
catgccacttgggtatttctgaaactttcattcgtctatacatttatgctattgattttt     180
tactaatttccagcatattttccaatctgtcactcaaaatctttttttattataaaccgtg    240
ttcttgaacacactaaaaagaacaagaaaatggaaatagaaaaattcattaaatctttag    300
caagaaaagcgaagttaggcgggcgttacagcacagccaatacctacctctacactttgc    360
acagttttcagaagtttgcgggaaaagcctcactgacttttgaagagatcactcccgaga    420
gtatcaaggagtacgagcaatacttaatcctcaacgggaaacggtacaacacgatctcgc    480
tctacatgcgcatgttgcgttccatctgcaatcaggcatcggagcagaacatagcttcgc    540
tcaacacccgcgagctgtttgagaatgtttttatcggcaacgaacccactgccaagcgtg    600
ccatctcacccgtcctcatttcccgcctgctcgaagcagatttcagcaagaacagccggc    660
tcgattttgcccgcgacctcttcttgctaagcttctacctgaggggaatcccgtttgtcg    720
acctggtacatctccgcaagaccgatgtgcagggaaacatgctcgtttatttccgccaga    780
aaacgggacagcaacttacggtaatcatagaaaactgcgccaaagtgatcttgcgtaagt    840
atgcctcgctttgcaaagaatccgtctatctgctgcccgtcatcagcgcagccggagagg    900
aggggcacaagcagtaccgaagtgcattgagggtatacaaacaaacgcctcaaccagatat    960
ccggaatactgaaattgaagactccgctgacctcttatgtggcacgccacagttgggcga   1020
ccacggccctgcagaaagggttccggtttcagtgatcagtgcaggaatggggcatgctt    1080
cagagaaggtgacatacatttatctggcatcttttgataacaaaacgctcagtaacgcaa    1140
ataaaaaagtgattgccgccgtgagatttaagaaagaggaggaggagtgataatagctgt    1200
tctcttacttattaggtaatagaacagattcatttgttttatcgctgcaaaaatagagat    1260
aataattgaaactccacaaacaaaatgataatttcttttctataaaagtggattataacc    1320
agttgaagtatcagtttgaaataatttattcacttaatagaaatattagtcataattcct    1380
gtttgatgtaattactcaaacaggagtttacaatttgcaataatttgacatcagaattat    1440
ataatccagcccctgttttatgtttagttaacctctaaaagttatatttcatatctttc    1500
gctattccgcattctattacctaataagtaagggatcactttgttctattacctaataag    1560
taagggaacaaattgcaatgcacacagcaagatggtagttattcaaacattaacgacaac    1620
tatcgcaaacatttctaaaagtacagtatgaaacaggtattgcggttcaataaagtcatt    1680
aaaaggattgtattcaccggagatctcattctcttgaatggcacctttctgtccttgtac    1740
accctattggggagcaaattttttgcagatccattcattcactcacttccccaagtactg    1800
gtattgctcaacttatgctacctggttagcaacatgtcttcaggtatcatattgcaccgc    1860
cgtgtagtacgtcccgagcaaatcgtatggcgtgccttacgcaacagtgcgggacacgcc    1920
ttgttttttcctgcgcgctcacctttggaaacttcggcatcctttccgcccgcttttc     1980
ttactgttctacattgcgttcactctgctgttggtttgttaccggttattgttccgcaag    2040
atcctgaagtcctatcgtaagcatggaggcaactcccgcagcatcattctggtgggaagc    2100
aatagcaatataatcgaactctaccatcaaatgacggacgacgtcacttccggattccgt    2160
gtcatcggctactttgacgaccagccaggcagccgcttccccgaaaaggtgaactatctg    2220
ggaaacccggtaagattgtggaccgcctgaagcagggaggagtcgagcaggtttattgt    2280
tgcctgccttcggcccgcagcgaagagattctccccatcatcgactattgcgaaaatcac    2340
ctgatacgcttttcagtgtccccaacgtgcgcagctatctgaagcggcgcatgtacttc    2400
gagctcctgggcaacgtgcccgtactctgcatccgccaggagccgctcagttttgccgaa    2460
aaccgattcaggaagcgtgtgttcgacatcgctttctcgctcttgtttctttgcaccctc    2520
ttccccattatctatgtcat                                           2540
```

METHOD FOR OVEREXPRESSION OF ZWITTERIONIC POLYSACCHARIDES

RELATED APPLICATIONS

This application is a continuation of U.S. patent application Ser. No. 10/388,390, filed Mar. 13, 2003, now issued as U.S. Pat. No. 7,166,455, which claims benefit under 35 U.S.C. §119(e) of U.S. provisional application Ser. No. 60/364,168, filed Mar. 13, 2002, the entire contents of both of which are hereby incorporated by reference.

GOVERNMENT RIGHTS

This invention was funded in part under National Institutes of Health Grant No. AI44193. The government may retain certain rights in the invention.

FIELD OF THE INVENTION

The invention relates to compositions and methods for the production and isolation of capsular polysaccharides which have been reported to have immunomodulatory effects. Specifically, the invention relates to compositions and methods for the production and isolation of capsular polysaccharide A (PSA) of *Bacteroides fragilis* (*B. fragilis*).

BACKGROUND OF THE INVENTION

Capsular polysaccharide A (PSA) of *Bacteroides fragilis* NCTC9343 has been reported to be an immunomodulator with therapeutic and preventative applications. U.S. Pat. Nos. 5,679,654 and 5,700,787; Tzianabos A O et al. (2000) *J Biol Chem* 275:6733-40. It was recently reported that in addition to PSA, *B. fragilis* NCTC9343 synthesizes at least seven other capsular polysaccharide (PSB-PSH). Krinos C M et al. (2001) *Nature* 414:555-558. It has also recently been reported that expression of seven of these eight capsular polysaccharides of *B. fragilis* are variable due to phase variation dictated by inversion of DNA segments containing the promoters of each of the polysaccharide biosynthesis loci. Krinos C M et al., supra. The fact that this strain synthesizes so many polysaccharides makes purification of PSA from this strain very laborious. This, coupled with the variable expression of PSA due to its phase variation, often results in a very low yield of PSA following extensive procedures for its purification. Scaled-up purification of PSA for preventative or therapeutic applications thus presents technical obstacles.

SUMMARY OF THE INVENTION

The invention arises in part from the discovery by the present inventors of methods for controlling the phase variation of seven of the eight known capsular polysaccharides of *B. fragilis*, PSA, PSB, PSD, PSE, PSF, PSG, and PSH. It was surprisingly discovered that inactivation of a novel gene, res02 (also denoted mpi, multiple promoter invertase), has the effect of locking the invertible promoters of each of the capsular polysaccharide biosynthesis loci in either an "on" orientation or an "off" orientation. When an invertible promoter of a capsular polysaccharide is in an on orientation, the promoter is transcriptionally active with respect to the polysaccharide biosynthesis locus associated with the biosynthesis of the capsular polysaccharide. Conversely, when an invertible promoter of a capsular polysaccharide is in an off orientation, the promoter is transcriptionally inactive with respect to the polysaccharide biosynthesis locus associated with the biosynthesis of the capsular polysaccharide. By locking the promoters and then selecting for bacterial cells constitutively expressing only a particular capsular polysaccharide, or expressing only a restricted set of capsular polysaccharides including the particular capsular polysaccharide, it was discovered according to the instant invention that it was now possible to increase the yield of the particular capsular polysaccharide. Thus, it was discovered according to the instant invention that it is now possible to generate and select mutant strains of *B. fragilis* that constitutively express any combination of selected capsular polysaccharides and not others. Furthermore, using this method it is now possible to generate and select mutant strains of *B. fragilis* that constitutively express only one particular capsular polysaccharide, e.g., PSA, and no other capsular polysaccharide. Because each selected mutant strain is rendered incapable of phase variation, the amount of selected polysaccharide, e.g., PSA, made by each cell is increased compared to wild type. In addition, because a selected mutant strain expresses only a single capsular polysaccharide, or it expresses only a desired combination of capsular polysaccharides, purification of capsular polysaccharide is greatly simplified and more efficient.

The invention also relates in part to a second novel gene, inv19, located adjacent to res02 and believed by the applicants also to be involved in controlling the expression of capsular polysaccharides in *B. fragilis*. Unlike res02, inactivation or deletion of inv19 does not appear to result in locking the phase variable promoters of capsular polysaccharide biosynthesis loci. However, it was discovered according to the instant invention that deletion of both res02 and inv19 can produce a genotype different from res02 deletion alone. For example, in one instance a res02 deletion alone did not express PSC, while a double res02/inv19 deletion did express PSC.

As detailed below, the present invention thus includes methods for producing and selecting novel mutant strains of *B. fragilis* that constitutively express only particular capsular polysaccharides; compositions directed to the novel mutant strains of *B. fragilis* that constitutively express only particular capsular polysaccharides; improved methods for purification of individual capsular polysaccharides; and novel compositions directed to the res02 and inv19 genes and their gene products.

It is believed that the novel res02 polypeptide encoded by the novel res02 gene functions as an invertase for nucleic acid sequences having specific structural characteristics. The specific structural characteristics include the presence of inverted repeat sequences flanking a central sequence, where the inverted repeat sequences have a particular sequence specifically recognized by the res02 polypeptide.

In one aspect the invention provides an isolated nucleic acid molecule related to res02. The nucleic acid according to this aspect includes a nucleotide sequence selected from the group consisting of: (a) a nucleotide sequence as set forth in SEQ ID NO:1; (b) a nucleotide sequence encoding a polypeptide as set forth in SEQ ID NO:2; (c) a nucleotide sequence which hybridizes under stringent conditions to a complement of (a) or (b); and (d) a nucleotide sequence complementary to any of (a)-(c). In one embodiment the nucleic acid molecule is a nucleotide sequence as set forth in SEQ ID NO:1. In one embodiment the nucleic acid molecule is a nucleotide sequence encoding a polypeptide as set forth in SEQ ID NO:2. A nucleotide sequence encoding a polypeptide as set forth in SEQ ID NO:2 includes a nucleotide sequence that differs from the nucleotide sequence as set forth in SEQ ID NO:1 in codon sequence due to degeneracy of the genetic code.

In another aspect the invention provides an isolated nucleic acid molecule related to res02. The nucleic acid according to this aspect includes a nucleotide sequence selected from the group consisting of: (a) a nucleotide sequence encoding a polypeptide which is at least about 70 percent identical to a polypeptide as set forth in SEQ ID NO:2, wherein the encoded polypeptide has an activity of the polypeptide set forth in SEQ ID NO:2; (b) a nucleotide sequence encoding an allelic variant of a nucleotide sequence as set forth in SEQ ID NO:1 or (a); (c) a region of the nucleotide sequence of SEQ ID NO:1, (a), or (b) encoding a polypeptide fragment of at least about 9 amino acid residues, wherein the polypeptide fragment has an activity of the encoded polypeptide as set forth in SEQ ID NO:2, or is antigenic; (d) a region of the nucleotide sequence of SEQ ID NO:1, or any of (a)-(c) comprising a fragment of at least about 16 nucleotides; (e) a nucleotide sequence which hybridizes under moderately or highly stringent conditions to the complement of any of (a)-(d); and (f) a nucleotide sequence complementary to any of (a)-(d).

In yet another aspect the invention provides an isolated nucleic acid molecule related to res02. The nucleic acid according to this aspect includes a nucleotide sequence selected from the group consisting of: (a) a nucleotide sequence encoding a polypeptide as set forth in SEQ ID NO:2 with at least one conservative amino acid substitution, wherein the encoded polypeptide has an activity of the polypeptide set forth in SEQ ID NO:2; (b) a nucleotide sequence encoding a polypeptide as set forth in SEQ ID NO:2 with at least one amino acid insertion, wherein the encoded polypeptide has an activity of the polypeptide set forth in SEQ ID NO:2; (c) a nucleotide sequence encoding a polypeptide as set forth in SEQ ID NO:2 with at least one amino acid deletion, wherein the encoded polypeptide has an activity of the polypeptide set forth in SEQ ID NO:2; (d) a nucleotide sequence encoding a polypeptide as set forth in SEQ ID NO:2 which has a C- and/or N-terminal truncation, wherein the encoded polypeptide has an activity of the polypeptide set forth in SEQ ID NO:2; (e) a nucleotide sequence encoding a polypeptide as set forth in SEQ ID NO:2 with at least one modification selected from the group consisting of amino acid substitutions, amino acid insertions, amino acid deletions, C-terminal truncation, and N-terminal truncation, wherein the encoded polypeptide has an activity of the polypeptide set forth in SEQ ID NO:2; (f) a nucleotide sequence of any of (a)-(e) comprising a fragment of at least about 16 nucleotides; (g) a nucleotide sequence which hybridizes under moderately or highly stringent conditions to the complement of any of (a)-(f); and (h) a nucleotide sequence complementary to any of (a)-(e).

In another aspect the invention provides a vector including the res02 nucleic acid molecule of any of the aspects above.

In a further aspect the invention provides a host cell including any of the res02 vectors above.

In another aspect the invention provides an isolated polypeptide related to res02. The isolated polypeptide according to this aspect includes an amino acid sequence as set forth in SEQ ID NO:2.

In another aspect the invention provides an isolated polypeptide related to res02. The isolated polypeptide according to this aspect includes an amino acid sequence selected from the group consisting of: (a) an amino acid sequence for an ortholog of SEQ ID NO:2; (b) an amino acid sequence which is at least about 70 percent identical to the amino acid sequence of SEQ ID NO:2, wherein the polypeptide has an activity of the polypeptide set forth in SEQ ID NO:2; (c) a fragment of the amino acid sequence set forth in SEQ ID NO:2 comprising at least about 9 amino acid residues, wherein the fragment has an activity of the polypeptide set forth in SEQ ID NO:2, or is antigenic; and (d) an amino acid sequence for an allelic variant of the amino acid sequence as set forth in SEQ ID NO:2, (a), or (b).

In yet another aspect the invention provides an isolated polypeptide related to res02. The isolated polypeptide according to this aspect includes an amino acid sequence selected from the group consisting of: (a) the amino acid sequence as set forth in SEQ ID NO:2 with at least one conservative amino acid substitution, wherein the polypeptide has an activity of the polypeptide set forth in SEQ ID NO:2; (b) the amino acid sequence as set forth in SEQ ID NO:2 with at least one amino acid insertion, wherein the polypeptide has an activity of the polypeptide set forth in SEQ ID NO:2; (c) the amino acid sequence as set forth in SEQ ID NO:2 with at least one amino acid deletion, wherein the polypeptide has an activity of the polypeptide set forth in SEQ ID NO:2; (d) the amino acid sequence as set forth in SEQ ID NO:2 which has a C- and/or N-terminal truncation, wherein the polypeptide has an activity of the polypeptide set forth in SEQ ID NO:2; and (e) the amino acid sequence as set forth in SEQ ID NO:2 with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NO:2.

In certain embodiments the isolated polypeptide encoded by any of the foregoing res02 nucleic acid molecules has an activity of the polypeptide set forth in SEQ ID NO:2. Specifically, in certain embodiments the activity is promoter invertase activity.

The invention in another aspect provides a selective binding agent or fragment thereof which specifically binds the res02 polypeptide of any of the foregoing aspects. In one embodiment the selective binding agent or fragment thereof specifically binds the polypeptide comprising the amino acid sequence as set forth in SEQ ID NO:2 or a fragment thereof. In one embodiment the selective binding agent is an antibody or fragment thereof.

In yet another aspect the invention provides a fusion polypeptide comprising the res02 polypeptide of any of the foregoing aspects, fused to a heterologous amino acid sequence.

In a further aspect the invention provides an isolated nucleic acid molecule related to inv19. The nucleic acid according to this aspect includes a nucleotide sequence selected from the group consisting of: (a) a nucleotide sequence as set forth in SEQ ID NO:3; (b) a nucleotide sequence encoding a polypeptide as set forth in SEQ ID NO:4; (c) a nucleotide sequence which hybridizes under stringent conditions to a complement of (a) or (b); and (d) a nucleotide sequence complementary to any of (a)-(c). In one embodiment the nucleic acid molecule is a nucleotide sequence as set forth in SEQ ID NO:3. In one embodiment the nucleic acid molecule is a nucleotide sequence encoding a polypeptide as set forth in SEQ ID NO:4. A nucleotide sequence encoding a polypeptide as set forth in SEQ ID NO:4 includes a nucleotide sequence that differs from the nucleotide sequence as set forth in SEQ ID NO:3 in codon sequence due to degeneracy of the genetic code.

In another aspect the invention provides an isolated nucleic acid molecule related to inv19. The nucleic acid according to this aspect includes a nucleotide sequence selected from the group consisting of: (a) a nucleotide sequence encoding a polypeptide which is at least about 70 percent identical to a polypeptide as set forth in SEQ ID NO:4, wherein the encoded polypeptide has an activity of the polypeptide set forth in SEQ ID NO:4; (b) a nucleotide sequence encoding an allelic variant of a nucleotide sequence as set forth in SEQ ID NO:3 or (a); (c) a region of the nucleotide sequence of SEQ ID NO:3, (a), or (b) encoding a polypeptide fragment of at least about 9 amino acid residues, wherein the polypeptide fragment has an activity of the encoded polypeptide as set forth in SEQ ID NO:4, or is antigenic; (d) a region of the nucleotide sequence of SEQ ID NO:3, or any of (a)-(c) comprising a fragment of at least about 16 nucleotides; (e) a nucleotide sequence which hybridizes under moderately or highly stringent conditions to the complement of any of (a)-(d); and (f) a nucleotide sequence complementary to any of (a)-(d).

In yet another aspect the invention provides an isolated nucleic acid molecule related to inv19. The nucleic acid according to this aspect includes a nucleotide sequence selected from the group consisting of: (a) a nucleotide sequence encoding a polypeptide as set forth in SEQ ID NO:4 with at least one conservative amino acid substitution, wherein the encoded polypeptide has an activity of the polypeptide set forth in SEQ ID NO:4; (b) a nucleotide sequence encoding a polypeptide as set forth in SEQ ID NO:4 with at least one amino acid insertion, wherein the encoded polypeptide has an activity of the polypeptide set forth in SEQ ID NO:4; (c) a nucleotide sequence encoding a polypeptide as set forth in SEQ ID NO:4 with at least one amino acid deletion, wherein the encoded polypeptide has an activity of the polypeptide set forth in SEQ ID NO:4; (d) a nucleotide sequence encoding a polypeptide as set forth in SEQ ID NO:4 which has a C- and/or N-terminal truncation, wherein the encoded polypeptide has an activity of the polypeptide set forth in SEQ ID NO:4; (e) a nucleotide sequence encoding a polypeptide as set forth in SEQ ID NO:4 with at least one modification selected from the group consisting of amino acid substitutions, amino acid insertions, amino acid deletions, C-terminal truncation, and N-terminal truncation, wherein the encoded polypeptide has an activity of the polypeptide set forth in SEQ ID NO:4; (f) a nucleotide sequence of any of (a)-(e) comprising a fragment of at least about 16 nucleotides; (g) a nucleotide sequence which hybridizes under moderately or highly stringent conditions to the complement of any of (a)-(f); and (h) a nucleotide sequence complementary to any of (a)-(e).

In another aspect the invention provides a vector including the inv19 nucleic acid molecule of any of the aspects above.

In a further aspect the invention provides a host cell including any of the inv19 vectors above.

In another aspect the invention provides an isolated polypeptide related to inv19. The isolated polypeptide according to this aspect includes an amino acid sequence as set forth in SEQ ID NO:4.

In another aspect the invention provides an isolated polypeptide related to inv19. The isolated polypeptide according to this aspect includes an amino acid sequence selected from the group consisting of: (a) an amino acid sequence for an ortholog of SEQ ID NO:4; (b) an amino acid sequence which is at least about 70 percent identical to the amino acid sequence of SEQ ID NO:4, wherein the polypeptide has an activity of the polypeptide set forth in SEQ ID NO:4; (c) a fragment of the amino acid sequence set forth in SEQ ID NO:4 comprising at least about 9 amino acid residues, wherein the fragment has an activity of the polypeptide set forth in SEQ ID NO:4, or is antigenic; and (d) an amino acid sequence for an allelic variant of the amino acid sequence as set forth in SEQ ID NO:4, (a), or (b).

In yet another aspect the invention provides an isolated polypeptide related to inv19. The isolated polypeptide according to this aspect includes an amino acid sequence selected from the group consisting of: (a) the amino acid sequence as set forth in SEQ ID NO:4 with at least one conservative amino acid substitution, wherein the polypeptide has an activity of the polypeptide set forth in SEQ ID NO:4; (b) the amino acid sequence as set forth in SEQ ID NO:4 with at least one amino acid insertion, wherein the polypeptide has an activity of the polypeptide set forth in SEQ ID NO:4; (c) the amino acid sequence as set forth in SEQ ID NO:4 with at least one amino acid deletion, wherein the polypeptide has an activity of the polypeptide set forth in SEQ ID NO:4; (d) the amino acid sequence as set forth in SEQ ID NO:4 which has a C- and/or N-terminal truncation, wherein the polypeptide has an activity of the polypeptide set forth in SEQ ID NO:4; and (e) the amino acid sequence as set forth in SEQ ID NO:4 with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NO:4.

In certain embodiments the isolated polypeptide encoded by any of the foregoing inv19 nucleic acid molecules has an activity of the polypeptide set forth in SEQ ID NO:4.

The invention in another aspect provides a selective binding agent or fragment thereof which specifically binds the inv19 polypeptide of any of the foregoing aspects. In one embodiment the selective binding agent or fragment thereof specifically binds the polypeptide comprising the amino acid sequence as set forth in SEQ ID NO:4 or a fragment thereof. In one embodiment the selective binding agent is an antibody or fragment thereof.

In yet another aspect the invention provides a fusion polypeptide comprising the inv19 polypeptide of any of the foregoing aspects, fused to a heterologous amino acid sequence.

According to yet another aspect of the invention, a bacterial cell is provided in which res02 expression is disabled. The expression of res02 can be disabled by any of a number of possible mechanisms, including, but not limited to, alteration of the res02 gene sequence by an insertion or deletion mutation that causes either deletion, truncation, or frameshift of the translated product, or disruption of a res02 gene expression sequence, such that res02 is not expressed by the cell.

According to yet another aspect of the invention, a bacterial cell is provided in which inv19 expression is disabled. The expression of inv19 can be disabled by any of a number of possible mechanisms, including, but not limited to, alteration of the inv19 gene sequence by an insertion or deletion mutation that causes either deletion, truncation, or frameshift of the translated product, or disruption of an inv19 gene expression sequence, such that inv19 is not expressed by the cell.

In another aspect the invention provides a population of bacterial cells stably expressing a specific capsular polysaccharide, or only a limited set of capsular polysaccharides including the specific capsular polysaccharide, selected from the group consisting of: PSA, PSB, PSD, PSE, PSF, PSG, and PSH. In one embodiment the specific capsular polysaccharide is PSA. In certain embodiments the bacterial cells are *B. fragilis*, including *B. fragilis* NCTC9343. In one embodiment the bacterial cells are *B. fragilis* 9343res02mut44. In another embodiment the bacterial cells are *B. fragilis* 9343res02mut2.

The invention further provides a bacterial cell expressing a capsular polysaccharide selected from the group consisting of: PSA, PSB, PSD, PSE, PSF, PSG, and PSH, wherein a promoter controlling expression of the capsular polysaccharide is locked on. In one preferred embodiment the capsular polysaccharide is PSA. In some embodiments promoters controlling expression of each and every capsular polysaccharide selected from the group consisting of: PSB, PSD, PSE, PSF, PSG, and PSH are locked off. In some embodiments any one or combination of capsular polysaccharides selected from the group consisting of: PSA, PSB, PSD, PSE, PSF, PSG, and PSH is not expressed. Also in some embodiments a promoter controlling expression of any one or combination of capsular polysaccharides selected from the group consisting of: PSA, PSB, PSD, PSE, PSF, PSG, and PSH, wherein said any one or combination of capsular polysaccharides is not expressed, is locked off. In one embodiment res02 expression is disabled. In one embodiment inv19 expression is disabled. In one embodiment res02 expression and inv19 expression are both disabled. In one embodiment the bacterial cell according to any of the foregoing aspects is *B. fragilis*. In one embodiment the bacterial cell according to any of the foregoing aspects is *B. fragilis* NCTC9343. In one embodiment the bacterial cell is *B. fragilis* 9343res02mut44. In another embodiment the bacterial cell is *B. fragilis* 9343res02mut2.

According to yet another aspect, the invention provides a method for locking a phase-variable promoter of a capsular polysaccharide biosynthesis gene on. The method according to this aspect involves inactivating res02 in a bacterial cell to lock a phase-variable promoter of a biosynthesis gene for a capsular polysaccharide on.

In a further aspect the invention provides a method for affecting expression of a capsular polysaccharide biosynthesis gene. The method according to this aspect involves inactivating inv19 in a bacterial cell to affect expression of a biosynthesis gene for a capsular polysaccharide. In certain embodiments the method further involves selecting a bacterial cell expressing at least one capsular polysaccharide selected from the group consisting of: PSA, PSB, PSD, PSE, PSF, PSG, and PSH. In certain embodiments the method further involves selecting a bacterial cell expressing only one capsular polysaccharide selected from the group consisting of: PSA, PSB, PSD, PSE, PSF, PSG, and PSH. In one embodiment the one capsular polysaccharide is PSA.

The invention in another aspect provides an improved method for purifying PSA from a bacterial cell. The improvement involves inactivating res02 in the bacterial cell such that a promoter for PSA is locked on or off, and selecting a bacterial cell expressing PSA. In one embodiment the bacterial cell is *B. fragilis*. In one embodiment the cell is *B. fragilis* NCTC9343. In one particular embodiment the bacterial cell is *B. fragilis* 9343res02mut44. In another particular embodiment the bacterial cell is *B. fragilis* 9343res02mut2.

The invention according to yet another aspect further provides a method for producing a pure capsular polysaccharide. The method according to this aspect involves growing a population of bacterial cells stably expressing a specific capsular polysaccharide, or only a restricted set of capsular polysaccharides including the specific capsular polysaccharide, selected from the group consisting of: PSA, PSB, PSD, PSE, PSF, PSG, and PSH, and isolating the specific capsular polysaccharide from the population of bacterial cells to produce a pure capsular polysaccharide. In one embodiment a promoter controlling expression of any one or combination of capsular polysaccharides selected from the group consisting of: PSA, PSB, PSD, PSE, PSF, PSG, and PSH, excluding the specific capsular polysaccharide, is locked off. In one embodiment the specific expressed capsular polysaccharide is PSA. In one embodiment promoters controlling expression of each and every capsular polysaccharide selected from the group consisting of: PSB, PSD, PSE, PSF, PSG, and PSH, are locked off. In one embodiment the bacterial cells are *B. fragilis*. In one embodiment the bacterial cells are *B. fragilis* NCTC9343. In a particular embodiment the bacterial cells are *B. fragilis* 9343res02mut44. In another a particular embodiment the bacterial cells are *B. fragilis* 9343res02mut2.

In yet another aspect the invention provides a method of treating or preventing inflammatory bowel disease. The method according to this aspect involves administering to a subject in need of treatment for or prevention of inflammatory bowel disease an effective amount of a population of bacterial cells stably expressing a specific capsular polysaccharide to treat or prevent the inflammatory bowel disease. In one embodiment the specific capsular polysaccharide is PSA. In one embodiment the bacterial cells are *B. fragilis*. In one embodiment the bacterial cells are *B. fragilis* NCTC9343. In one embodiment the bacterial cells are *B. fragilis* 9343res02mut44 (mut44). In another embodiment the bacterial cells are *B. fragilis* 9343res02mut2 (mut2).

BRIEF DESCRIPTION OF THE DRAWINGS

FIG. 1 is the nucleotide sequence of res02 (SEQ ID NO:1).

FIG. 2 is the deduced amino acid sequence of res02 (SEQ ID NO:2).

FIG. 3 is the nucleotide sequence of inv19 (SEQ ID NO:3).

FIG. 4 is the deduced amino acid sequence of inv19 (SEQ ID NO:4).

FIG. 6 is the nucleotide sequence of Left Flank, inv19-D1→through←inv19-D2, 1,958 bp (SEQ ID NO:5).

FIG. 7 is the nucleotide sequence of Right Flank, inv19-D5→through←inv19-D6, 2,540 bp (SEQ ID NO:6).

DETAILED DESCRIPTION

Figure 5:
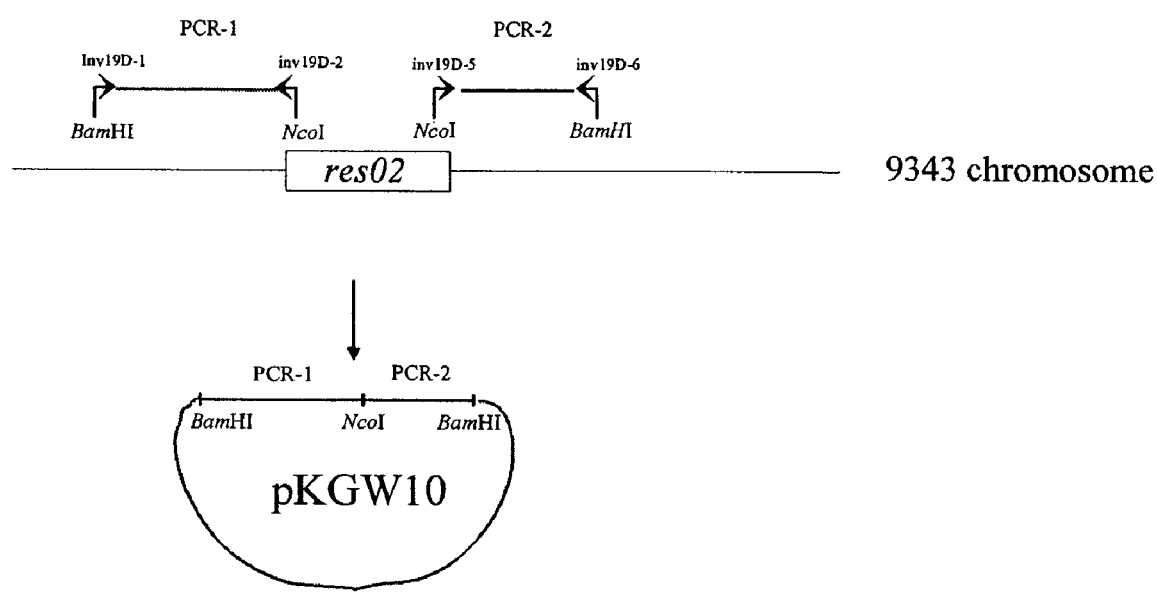
FIG. 5 is a diagram showing the construction of pKGW10 and mutation strategy used in deleting res02 from the *B. fragilis* NCTC9343 chromosome. The direction of translation of res02 is from right to left in the figure.

The technology described in this application has utilized the genetic information that the inventors have discovered about *B. fragilis* NCTC9343 to circumvent both the difficulty of purification of one capsular polysacharide from the other seven polysaccharides, and the low yield of a given capsular polysaccharide due to the phase variation in its expression. Importantly, the technology described in this application circumvents both the difficulty of purification of PSA from the other seven polysaccharides, and the low yield of PSA due to the phase variation in its expression.

In featured aspects of the invention, res02 is inactivated so that phase variation of the capsular polysaccharides is eliminated. The lack of res02 activity renders the invertible promoters for the polysaccharide biosynthesis loci locked in either the on or the off orientation. Selection of particular phenotypes then permits selection of mutants with the promoter of a selected capsular polysaccharide locked on and the promoters of other capsular polysaccharides locked off.

The terms "res02", "res02 gene", and "res02 nucleic acid molecule" refer to a nucleic acid molecule comprising or consisting of a nucleotide sequence as set forth in SEQ ID NO:1, a nucleotide sequence encoding the polypeptide as set forth in SEQ ID NO:2, and nucleic acid molecules as defined herein.

The terms "inv19", "inv19 gene", and "inv19 nucleic acid molecule" refer to a nucleic acid molecule comprising or consisting of a nucleotide sequence as set forth in SEQ ID NO:3, a nucleotide sequence encoding the polypeptide as set forth in SEQ ID NO:4, and nucleic acid molecules as defined herein.

The terms "res02", "res02 polypeptide", and "res02 gene product" refer to a polypeptide comprising the amino acid sequence of SEQ ID NO:2 and related polypeptides. Related polypeptides include res02 polypeptide fragments, res02 polypeptide orthologs, res02 polypeptide variants, and res02 polypeptide derivatives, which possess at least one activity of the polypeptide as set forth in SEQ ID NO:2.

The terms "inv19", "inv19 polypeptide", and "inv19 gene product" refer to a polypeptide comprising the amino acid sequence of SEQ ID NO:4 and related polypeptides. Related polypeptides include inv19 polypeptide fragments, inv19 polypeptide orthologs, inv19 polypeptide variants, and inv19 polypeptide derivatives, which possess at least one activity of the polypeptide as set forth in SEQ ID NO:4.

Methods and Compositions for Overexpressing Capsular Polysaccharides

A bacterial cell in which "res02 expression is disabled" is a viable bacterial cell in which the level of functional res02 polypeptide is negligible compared to the level of functional res02 polypeptide normally expressed by the bacterial cell under the same conditions. The expression can be disabled by the introduction or presence of a mutation in the res02 gene that results in a nonfunctional res02 gene product or no functional res02 gene product. Such mutations include those involving at least one missense mutation, nonsense mutation, truncation mutation, insertion mutation, or deletion mutation, or any combination thereof, involving the res02 open reading frame (ORF). In some embodiments mutations resulting in disabled res02 expression include at least one truncation, insertion, or deletion mutation, or any combination thereof, involving the res02 promoter. In some embodiments res02 expression is disabled through manipulation of factors upstream of the expression of res02. For example, transcriptional activators, signal transduction, and global regulators can influence expression of res02. See, for example, Gally D L et al. (1993) *J Bacteriol* 175:6186-93; Blomfield I C et al. (1993) *J Bacteriol* 175:27-36; Dorman C J et al. (1987) *J Bacteriol* 169:3840-43; Eisenstein B I et al. (1987) *Proc Natl Acad Sci USA* 84:6506-10. In one embodiment, a bacterial cell in which res02 expression is disabled has a chromosomal deletion of the res02 gene.

For example, a bacterial cell in which res02 expression is disabled can be a cell in which there is a deletion of any one or combination of the first, second, third, fourth, fifth, sixth, and so on, nucleotides shown in SEQ ID NO:1. In one embodiment the deletion occurs nearer to the 5' end than to the 3' end. For example, deletion of the first, second or third nucleotide shown in SEQ ID NO:1 obliterates the "atg" start codon at position 1 and moves the first "atg" start codon to position 67 of SEQ ID NO:1, generating an ORF that encodes amino acids 23-197 shown in SEQ ID NO:2. As another example, deletion of the fourth nucleotide shown in SEQ ID NO:1 maintains the original "atg" start codon at position 1 but introduces a number of adjacent and nearby stop codons.

As a further example, a bacterial cell in which res02 expression is disabled can be a cell in which there is an insertion of one or more nucleotides following any one or combination of the first, second, third, fourth, fifth, sixth, and so on, nucleotides shown in SEQ ID NO:1. For example, the insertion can be an insertion of an in-frame stop codon (taa, tag, tga) in SEQ ID NO:1. As a further example, the insertion can be a polynucleotide, e.g., a polynucleotide sequence that encodes an exogenous gene product. In one embodiment the insertion occurs nearer to the 5' end than to the 3' end.

The deletion or insertion can be accomplished by homologous recombination.

Homologous recombination is a technique originally developed for targeting genes to induce or correct mutations in transcriptionally active genes. Kucherlapati R S (1989) *Prog Nucleic Acid Res Mol Biol* 36:301-10. The basic technique was developed as a method for introducing specific mutations into specific regions of the mammalian genome (Thomas K R et al. (1986) *Cell* 44:419-28; Thomas K R et al. (1987) *Cell* 51:503-12; Doetschman T et al. (1988) *Proc Natl Acad Sci USA* 85:8583-87) or to correct specific mutations within defective genes (Doetschman T et al. (1987) *Nature* 330:576-78). Exemplary homologous recombination techniques are described in U.S. Pat. No. 5,272,071; European Patent Nos. 9193051 and 505500; and PCT/US90/07642 (PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Homologous recombination can also be used to delete a region of genomic DNA. In this instance the targeting DNA is a nucleotide sequence that is complementary (homologous) to regions of the genomic DNA flanking that which is to be deleted. The targeting DNA is usually at least one kilobase (1 kb) long for each flanking region, and more preferably it is closer to 2 kb for each flanking region. If this complementary strand is put in contact with the parental strand during the DNA replication process, it is incorporated into the newly synthesized strand as a result of recombination. As a result of the proofreading function, it is possible for the new sequence of DNA, lacking the original genomic sequence between the homologous flanking regions, to serve as the template. Thus, the transferred DNA is incorporated into the genome.

Deletion by homologous recombination involves double crossover allelic exchange. In this method a first recombination event occurs with one flank region, and then a second recombination event occurs with the opposite flank. As a result, double crossover homologous exchange results in two groups of cells, those which are deletion mutants and those which are wild type. The determination of whether a particular cell is wild type or a deletion mutant can be accomplished by screening for the wild type gene or wild type gene product, or direct screening for the chromosomal deletion.

A bacterial cell in which "inv19 expression is disabled" is a viable bacterial cell in which the level of functional inv19 polypeptide is negligible compared to the level of functional inv19 polypeptide normally expressed by the bacterial cell under the same conditions. The expression can be disabled by the introduction or presence of a mutation in the inv19 gene that results in a nonfunctional inv19 gene product or no functional inv19 gene product. Such mutations include those involving at least one missense mutation, nonsense mutation, truncation mutation, insertion mutation, or deletion mutation, or any combination thereof, involving the inv19 open reading frame (ORF). In some embodiments mutations resulting in disabled inv19 expression include at least one truncation, insertion, or deletion mutation, or any combination thereof, involving the inv19 promoter. In some embodiments inv19 expression is disabled through manipulation of factors upstream of the expression of inv19. For example, transcriptional activators, signal transduction, and global regulators can influence expression of res02. See, for example, Gally D L et al. (1993) *J Bacteriol* 175:6186-93; Blomfield I C et al. (1993) *J Bacteriol* 175:27-36; Dorman C J et al. (1987) *J Bacteriol* 169:3840-43; Eisenstein B I et al. (1987) *Proc Natl Acad Sci USA* 84:6506-10. In one embodiment, a bacterial cell in which inv19 expression is disabled has a chromosomal deletion of the inv19 gene.

For example, a bacterial cell in which inv19 expression is disabled can be a cell in which there is a deletion of any one or combination of the first, second, third, fourth, fifth, sixth, and so on, nucleotides shown in SEQ ID NO:3. In one embodiment the deletion occurs nearer to the 5' end than to the 3' end.

As a further example, a bacterial cell in which inv19 expression is disabled can be a cell in which there is an insertion of one or more nucleotides following any one or combination of the first, second, third, fourth, fifth, sixth, and so on, nucleotides shown in SEQ ID NO:3. For example, the insertion can be an insertion of an in-frame stop codon (taa, tag, tga) in SEQ ID NO:3. As a further example, the insertion can be a polynucleotide, e.g., a polynucleotide sequence that encodes an exogenous gene product. In one embodiment the insertion occurs nearer to the 5' end than to the 3' end.

The deletion or insertion can be accomplished by homologous recombination.

A "population of bacterial cells" is a culture of bacterial cells. The culture can be liquid culture, semi-solid culture, e.g., in gelatin, or a culture on solid medium, e.g., on nutrient-supplemented agar. Examples of these various types of bacterial culture are well-known by those of skill in the art. A liquid culture can be in a test tube, flask, roller bottle, bioreactor, or other suitable container, preferably with controlled conditions of temperature, aeration, and agitation. The volume of a liquid culture can range from less than 1 mL to 10 L or more. In one embodiment the population of bacterial cells derives from a single bacterium, i.e., it is a clone.

A "bacterial cell expressing a capsular polysaccharide" refers to the detectable phenotype of a bacterial cell with respect to the capsular polysaccharide. The phenotype can be concordant or discordant with genotype. For example, a bacterial cell with a promoter for PSE locked in the on orientation may or may not express PSE. Of course, a bacterial cell with a promoter for PSE locked in the off orientation generally will not express PSE. The genotype can conveniently be assessed by polymerase chain reaction, restriction endonuclease digestion, direct sequencing, or any other method suitable for determining or inferring the sequence of a relevant segment of chromosomal DNA or RNA. The phenotype can conveniently be assessed by Western immunoblot, immunoaffinity, or other suitable assay using antibodies or other capsular polysaccharide binding agents specific for the particular capsular polysaccharide to be assayed. The antibodies can be in the form of monospecific or defined specificity antisera, polyclonal antibodies, monoclonal antibodies, polysaccharide-specific binding fragments of the foregoing antibodies, and derivatives thereof.

A "bacterial cell stably expressing a specific capsular polysaccharide" refers to a bacterial cell expressing a particular capsular polysaccharide without phase variation of its expression. A "population of bacterial cells stably expressing a specific capsular polysaccharide" refers to a population of bacterial cells expressing a particular capsular polysaccharide without phase variation of its expression. In certain embodiments the specific capsular polysaccharide is the only capsular polysaccharide expressed by the bacterial cell or by the population of bacterial cells. The absence of phase variation can reflect the inactivation of res02 such that the normally invertible promoter for the polysaccharide biosynthesis gene is locked in its on orientation.

A "promoter controlling expression of a capsular polysaccharide" as used herein refers to a nontranscribed genetic element associated with and controlling the transcription of a capsular polysaccharide biosynthesis gene. The capsular polysaccharide biosynthesis gene can occur as part of a polycistronic capsular polysaccharide biosynthesis locus. A given promoter can regulate transcription of one or more capsular polysaccharide biosynthesis genes within the associated capsular polysaccharide biosynthesis gene locus. In one embodiment the promoter includes inverted repeat regions separated by intervening sequence. In one embodiment the promoter is contained between inverted repeat regions in the intervening sequence and is subject to inversion such that in one orientation the promoter is transcriptionally active ("on") with respect to the capsular polysaccharide biosynthesis gene, while in the opposite or flipped orientation the promoter is transcriptionally inactive ("off") with respect to the capsular polysaccharide biosynthesis gene. The inversion of the invertible promoter region between the inverted repeat regions is subject to control by a sequence-specific enzyme termed a recombinase or invertase. In one embodiment, the recombinase or invertase is res02 or inv19. The promoters for seven of the eight known capsular polysaccharides of *B. fragilis*, PSA, PSB, PSD, PSE, PSF, PSG, and PSH, have been reported to be flanked by inverted repeat regions and are subject to inversion. Krinos C M et al. (2001) *Nature* 414:555-58.

The downstream inverted repeat of each the seven capsular polysaccharides in *B. fragilis* is shown in Table 1. Sequence shown in bold print represents a consensus res02 recognition sequence necessary for promoter inversion.

TABLE 1

Characteristics of the inverted repeat (IR) regions upstream of the seven polysaccharide (PS) biosynthesis loci.

| PS LOCUS | SEQUENCE OF THE DOWNSTREAM IR | BASEPAIRS BETWEEN IRS | SEQ ID NO: |
| --- | --- | --- | --- |
| PSA | acgaacgtttttgaaaca | 193 | 7 |
| PSB | acgaacgtttttgaaaca | 181 | 7 |
| PSD | tagacgatcgtctattgaaaca | 189 | 8 |
| PSE | acgaacgtttttgaaaca | 168 | 7 |
| PSF | ttaaacgaacgtctattgaaacact | 187 | 9 |
| PSG | gttcaaatagacgaacgtt | 174 | 10 |
| PSH | acgaacgtttttgaaaca | 192 | 7 |
| PSC | None | | |

A "phase-variable promoter of a capsular polysaccharide biosynthesis gene" refers to A "phase-variable promoter of a capsular polysaccharide biosynthesis gene" refers to a promoter for a capsular polysaccharide biosynthesis gene that, as just described, includes inverted repeat regions separated by intervening sequence and is subject to inversion such that in one orientation the promoter is transcriptionally active ("on") with respect to the capsular polysaccharide biosynthesis genes, while in the opposite orientation the promoter is transcriptionally inactive ("off") with respect to the capsular polysaccharide biosynthesis genes. Phase variation results in the variable expression of the capsular polysaccharide in response to the orientation of the invertible promoter. This phase variation normally can occur within a given cell over time, for reasons that are not yet understood. Seven of the eight known capsular polysaccharides of B. fragilis, PSA, PSB, PSD, PSE, PSF, PSG, and PSH, are subject to phase variation. For the eight known capsular polysaccharides, the phenotype of a given cell theoretically can vary over time among any of $2^8$ (256) phenotypes. However, as disclosed herein, the phase variation among the capsular polysaccharides can be fixed or locked through disabling of the promoter inversion mechanism that underlies the phase variation.

A promoter controlling expression of a capsular polysaccharide is "locked on" when the invertible promoter is in its transcriptionally active orientation and it cannot invert to the transcriptionally inactive orientation. The promoter can be locked on because a sequence-specific enzyme that normally inverts the promoter is not present or is otherwise disabled. Alternatively, the promoter can be locked on because at least one inverted repeat flanking the invertible region of the promoter is altered, e.g., deleted, so that the inversion is not possible.

A promoter controlling expression of a capsular polysaccharide is "locked off" when the invertible promoter is in its transcriptionally inactive orientation and it cannot invert to the transcriptionally active orientation. The promoter can be locked off because a sequence-specific enzyme that normally inverts the promoter is not present or is otherwise disabled. Alternatively, the promoter can be locked off because at least one inverted repeat flanking the invertible region of the promoter is altered, e.g., deleted, so that the inversion is not possible.

The phrase "inactivating res02 in a bacterial cell to lock a phase-variable promoter of a biosynthesis gene for a capsular polysaccharide" refers to any intervention that renders inversion of a phase-variable promoter of a biosynthesis gene for a capsular polysaccharide of the bacterial cell by res02 gene product impossible. The intervention can typically involve deletion of the res02 gene as described herein. Other interventions are also contemplated, including introduction of other res02 gene mutations that result in nonfunctional res02 gene products, introduction of res02 antisense nucleic acid or other agent that bind to res02 nucleic acid molecule, as well as introduction into the bacterial cell of agents that can interfere with the function of otherwise functional res02 gene product.

The phrase "inactivating inv19 in a bacterial cell to lock a phase-variable promoter of a biosynthesis gene for a capsular polysaccharide" refers to any intervention that renders inversion of a phase-variable promoter of a biosynthesis gene for a capsular polysaccharide of the bacterial cell by inv19 gene product impossible. The intervention can typically involve deletion of the inv19 gene as described herein. Other interventions are also contemplated, including introduction of other inv19 gene mutations that result in nonfunctional inv19 gene products, introduction of inv19 antisense nucleic acid or other agent that bind to inv19 nucleic acid molecule, as well as introduction into the bacterial cell of agents that can interfere with the function of otherwise functional inv19 gene product.

A "pure capsular polysaccharide" refers to a capsular polysaccharide of the invention that (1) has been separated from at least about 50 percent of proteins, lipids, carbohydrates, or other materials with which it is naturally found when total capsular polysaccharide is isolated from the source cells, and (2) is substantially free of all other capsular polysaccharides. "Substantially free of all other capsular polysaccharides" means the capsular polysaccharide of interest represents at least 80 percent of all capsular polysaccharides present. Preferably, the capsular polysaccharide of interest represents at least 85 percent, more preferably at least 90 percent, even more preferably at least 95 percent, and most preferably at least 98 percent, of all capsular polysaccharides present. In one embodiment, a pure capsular polysaccharide of the present invention is substantially free from any contaminants that are found in its natural environment that would interfere with its therapeutic, diagnostic, prophylactic or research use.

"Inflammatory bowel disease" refers to a group of chronic inflammatory disorders of unknown or autoimmune cause involving the gastrointestinal tract. These disorders are well known in the medical arts and include two principal categories, ulcerative colitis and Crohn's disease. Ulcerative colitis characteristically occurs as continuous lesions in the colon involving the mucosa alone, whereas Crohn's disease characteristically occurs as discontinuous lesions anywhere in the gastrointestinal tract, involving inflammation of all layers of the bowel wall. While the etiology of inflammatory bowel disease remains uncertain, there is evidence to suggest there may be an underlying infectious etiology, and effective treatments include the use of local or systemic immunomodulatory agents. See Glickman R M in: Harrison's Principles of Internal Medicine, $14^{th}$ Ed., Fauci A S et al., eds., New York: McGraw-Hill, 1998, Chapter 286.

It is believed by the inventors that live or viable bacteria overexpressing PSA can be used to treat or prevent inflammatory bowel disease. The bowel is normally colonized by bacteria of many species, including B. fragilis. Therefore introduction into the bowel of live or viable bacteria overexpressing PSA is expected to be well tolerated. However, due to the previously described beneficial effects of PSA in inflammatory bowel disease, believed to be related to the ability of PSA to induce the anti-inflammatory cytokine interleukin-10 (IL-10), and the ability these bacteria to overexpress PSA, it is expected that these live or viable bacteria can be introduced into the bowel and thus treat and prevent inflammatory bowel disease. The live or viable bacteria overexpressing PSA can be administered to subjects in need of treatment for inflammatory bowel disease by mouth or per rectum. Their effect can be determined by following disease activity in the usual manner. Furthermore, the live or viable bacteria overexpressing PSA can be administered in conjunction with any other therapeutic agent useful in the treatment of inflammatory bowel disease, except, of course, antibiotics to which the live or viable bacteria overexpressing PSA are sensitive. Viable bacteria specifically include lyophylized bacteria that are capable of growth upon their return to suitable conditions.

Res02 and Inv19 Nucleic Acids and Polypeptides

The term "polypeptide allelic variant" refers to one or several possible naturally occurring alternate forms of a gene occupying a given locus on a chromosome of an organism or a population of organisms.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide to which it is not linked in nature, or (4) does not occur in nature as part of a larger polynucleotide sequence. Preferably, the isolated nucleic acid molecule of the present invention is substantially free from any other nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the natural bases (adenine, cytosine, guanine, thymine, uracil) as well as base analogs of DNA and RNA such as, but not limited to, 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, 2,6-diaminopurine, and any combination thereof. In some embodiments the nucleic acid sequence or nucleic acid molecule can have a modified backbone, e.g., a backbone characterized by at least one internucleoside linkage that is other than a phosphodiester bond. In one embodiment the modified backbone includes at least one stabilized internucleoside linkage, e.g., a phosphorthioate or phosphorodithioate linkage.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of gene expression sequence and coding sequence wherein transcriptional and/or translational control elements of the gene expression sequence and open reading frame of the coding sequence are covalently linked in such a way as to place the expression or transcription and/or translation of the coding sequence under the influence or control of the gene expression sequence. Thus, two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a res02 or inv19 nucleic acid sequence if the gene expression sequence were capable of effecting transcription of the res02 or inv19 nucleic acid sequence such that the resulting transcript is translated into the desired protein or polypeptide. A gene expression sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence. Furthermore, an enhancer can be upstream or downstream of the coding sequence, and the enhancer need not be contiguous with the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "res02 polypeptide fragment" refers to a polypeptide that comprises a truncation at the amino-terminus and/or a truncation at the carboxyl-terminus of the polypeptide as set forth in SEQ ID NO:2. The term "res02 polypeptide fragment" also refers to amino-terminal and/or carboxyl-terminal truncations of res02 polypeptide orthologs, res02 polypeptide derivatives, or res02 polypeptide variants, or to amino-terminal and/or carboxyl-terminal truncations of the polypeptides encoded by res02 polypeptide allelic variants or res02 polypeptide splice variants. In certain embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise contiguous amino acids numbering about 187, or about 177, or about 147, or about 122, or about 97, or down to about 9, including every integer therebetween. Such res02 polypeptide fragments can optionally comprise an amino-terminal methionine residue. It will be appreciated that such fragments can be used, for example, to generate antibodies to res02 polypeptides.

The term "inv19 polypeptide fragment" refers to a polypeptide that comprises a truncation at the amino-terminus and/or a truncation at the carboxyl-terminus of the polypeptide as set forth in SEQ ID NO:4. The term "inv19 polypeptide fragment" also refers to amino-terminal and/or carboxyl-terminal truncations of inv19 polypeptide orthologs, inv19 polypeptide derivatives, or inv19 polypeptide variants, or to amino-terminal and/or carboxyl-terminal truncations of the polypeptides encoded by inv19 polypeptide allelic variants or inv19 polypeptide splice variants. In certain embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise contiguous amino acids numbering about 296, or about 286, or about 256, or about 231, or about 206, or down to about 9, including every integer therebetween. Such inv19 polypeptide fragments can optionally comprise an amino-terminal methionine residue. It will be appreciated that such fragments can be used, for example, to generate antibodies to inv19 polypeptides.

The term "res02 polypeptide ortholog" refers to a polypeptide from another species that corresponds to res02 polypeptide amino acid sequence as set forth in SEQ ID NO:2.

The term "inv19 polypeptide ortholog" refers to a polypeptide from another species that corresponds to inv19 polypeptide amino acid sequence as set forth in SEQ ID NO:4.

The term "res02 polypeptide variants" refers to res02 polypeptides comprising amino acid sequences having one or more amino acid sequence substitutions, deletions (such as internal deletions and/or res02 polypeptide fragments), and/or additions (such as internal additions and/or res02 fusion polypeptides) as compared to the res02 polypeptide amino acid sequence set forth in SEQ ID NO:2. Variants can be naturally occurring (e.g., res02 polypeptide allelic variants and res02 polypeptide orthologs) or artificially constructed. Such res02 polypeptide variants can be prepared from the corresponding nucleic acid molecules having a DNA sequence that varies accordingly from the DNA sequence as set forth in SEQ ID NO:1. In certain embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions can be conservative, or non-conservative, or any combination thereof.

The term "inv19 polypeptide variants" refers to inv19 polypeptides comprising amino acid sequences having one or more amino acid sequence substitutions, deletions (such as internal deletions and/or inv19 polypeptide fragments), and/or additions (such as internal additions and/or inv19 fusion polypeptides) as compared to the inv19 polypeptide amino acid sequence set forth in SEQ ID NO:4. Variants can be naturally occurring (e.g., inv19 polypeptide allelic variants and inv19 polypeptide orthologs) or artificially constructed. Such inv19 polypeptide variants can be prepared from the corresponding nucleic acid molecules having a DNA sequence that varies accordingly from the DNA sequence as set forth in SEQ ID NO:3. In certain embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions can be conservative, or non-conservative, or any combination thereof.

The term "res02 polypeptide derivatives" refers to the polypeptide as set forth in SEQ ID NO:2, res02 polypeptide fragments, res02 polypeptide orthologs, or res02 polypeptide variants, as defined herein, that have been chemically modified. The term "res02 polypeptide derivatives" also refers to the polypeptides encoded by res02 polypeptide allelic variants, as defined herein, that have been chemically modified.

The term "inv19 polypeptide derivatives" refers to the polypeptide as set forth in SEQ ID NO:4, inv19 polypeptide fragments, inv19 polypeptide orthologs, or inv19 polypeptide variants, as defined herein, that have been chemically modified. The term "inv19 polypeptide derivatives" also refers to the polypeptides encoded by inv19 polypeptide allelic variants, as defined herein, that have been chemically modified.

The term "res02 fusion polypeptide" refers to a fusion of one or more amino acids (such as a heterologous protein or peptide) at the amino- or carboxyl-terminus of the polypeptide as set forth in SEQ ID NO:2, res02 polypeptide fragments, res02 polypeptide orthologs, res02 polypeptide variants, or res02 derivatives, as defined herein. The term "res02 fusion polypeptide" also refers to a fusion of one or more amino acids at the amino- or carboxyl-terminus of the polypeptide encoded by res02 polypeptide allelic variants or res02 polypeptide splice variants, as defined herein.

The term "inv19 fusion polypeptide" refers to a fusion of one or more amino acids (such as a heterologous protein or peptide) at the amino- or carboxyl-terminus of the polypeptide as set forth in SEQ ID NO:4, inv19 polypeptide fragments, inv19 polypeptide orthologs, inv19 polypeptide variants, or inv19 derivatives, as defined herein. The term "inv19 fusion polypeptide" also refers to a fusion of one or more amino acids at the amino- or carboxyl-terminus of the polypeptide encoded by inv19 polypeptide allelic variants or inv19 polypeptide splice variants, as defined herein.

The term "biologically active res02 polypeptides" refers to res02 polypeptides having at least one activity characteristic of the polypeptide comprising the amino acid sequence of SEQ ID NO:2. In one embodiment the activity is promoter invertase activity. In addition, a res02 polypeptide can be active as an immunogen; that is, the res02 polypeptide contains at least one epitope to which antibodies may be raised.

The term "biologically active inv19 polypeptides" refers to inv19 polypeptides having at least one activity characteristic of the polypeptide comprising the amino acid sequence of SEQ ID NO:4. In addition, an inv19 polypeptide can be active as an immunogen; that is, the inv19 polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). Percent identity with respect to nucleic acid molecules can be conveniently determined using a sequence alignment algorithm or computer program such as GAP, BLASTN, FASTA, BLASTA, BLASTX, BestFit, and the Smith-Waterman algorithm. Percent identity with respect to polypeptides can be conveniently determined using a sequence alignment algorithm or computer program such as GAP, BLASTP, FASTA, BLASTA, BLASTX, BestFit, and the Smith-Waterman algorithm.

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Except as used in connection with the term "isolated", the term "naturally occurring" or "native" when used in connection with biological materials such as nucleic acid molecules, polypeptides, host cells, and the like, refers to materials as they are found in nature and not manipulated by man. When used in connection with the term "isolated", the term "naturally occurring" or "native" when used in connection with biological materials such as nucleic acid molecules, polypeptides, host cells, and the like, refers to isolated materials sharing wild type structural features as they are found in nature. For example, an isolated naturally occurring res02 polypeptide is in one embodiment an isolated wild type res02 polypeptide having the sequence of SEQ ID NO:2. The term "non-naturally occurring" or "non-native" as used herein refers to a material that is not found in nature or that has been structurally modified or synthesized by man.

The term "effective amount" refers to that amount of a substance that is useful in accomplishing the purpose for which it is used. The term "therapeutically effective amount" refers to that amount of a substance that is useful in accomplishing the therapeutic effect for which it is used. Thus a therapeutically effective amount of a substance is that amount of the substance that, when administered to a subject to treat or prevent a condition or disease of the subject, prevents the onset of, alleviates the symptoms of, or stops the progression of the condition or disease of the subject.

The term "pharmaceutically acceptable carrier" or "physiologically acceptable carrier" as used herein refers to one or more formulation materials suitable for accomplishing or enhancing the delivery of an agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen can have one or more epitopes.

The term "selective binding agent" refers to a molecule or molecules having specificity for an antigen, e.g., a res02 or inv19 polypeptide. As used herein, the terms "specific" and "specificity" refer to the ability of the selective binding agents to bind to an antigen of interest and not to bind to other antigens.

The term "transduction" is used to refer to the transfer of genes from one bacterium to another, usually by a phage.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Sambrook et al, Molecular Cloning: A Laboratory Manual (2nd ed., Cold Spring Harbor Laboratory Press, 1989). Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA can recombine with that of the cell by physically integrating into a chromosome of the cell, can be maintained transiently as an episomal element without being replicated, or can replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic variants of the nucleic acid molecule of either SEQ ID NO:1 or SEQ ID NO:3, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in either SEQ ID NO:2 or SEQ ID NO:4.

Related nucleic acid molecules also include fragments of res02 or inv19 nucleic acid molecules which encode a polypeptide of at least about 9 contiguous amino acids, or about 50 amino acids, or about 75 amino acids, or about 100 amino acids, or about 150 amino acids, or about 200 amino acids, or more than about 200 amino acid residues of the res02 or inv19 polypeptide of either SEQ ID NO:2 or SEQ ID NO:4.

In addition, related res02 or inv19 nucleic acid molecules also include those molecules which comprise nucleotide sequences which hybridize under moderately or highly stringent conditions as defined herein with the fully complementary sequence of the res02 or inv19 nucleic acid molecule of either SEQ ID NO:1 or SEQ ID NO:3, respectively, or of a molecule encoding a polypeptide, which polypeptide comprises the amino acid sequence as shown in either SEQ ID NO:2 or SEQ ID NO:4, or of a nucleic acid fragment as defined herein, or of a nucleic acid fragment encoding a polypeptide as defined herein. Hybridization probes can be prepared using the res02 or inv19 sequences provided herein to screen cDNA, genomic or synthetic DNA libraries for related sequences. Regions of the DNA and/or amino acid sequence of res02 or inv19 polypeptide that exhibit significant identity to known sequences are readily determined using sequence alignment algorithms as described herein and those regions can be used to design probes for screening.

The term "nucleic acid fragment" refers to a nucleic acid molecule sharing in common with a sequence from which it derives any sequence of at least 16 contiguous bases that is at least one base shorter than the sequence from which it derives. The nucleic acid fragment can be 16, 17, 18, 19, 20, and so on, bases long, up to but not including the total number of bases of the sequence from which it derives. For example, in some embodiments a nucleic acid fragment of SEQ ID NO:1 is a 16-mer defined by bases 1-16, 2-17, 3-18, 4-19, and so on through bases 579-594 of SEQ ID NO:1. As a further example, in some embodiments a nucleic acid fragment of SEQ ID NO:1 is a 17-mer defined by bases 1-17, 2-18, 3-19, 4-120, and so on through bases 578-594 of SEQ ID NO:1. In certain preferred embodiments a nucleic acid fragment encodes an immunogenic peptide of a corresponding polypeptide encoded by the full length nucleic acid sequence from which the fragment is derived. Since immunogenic peptides are generally recognized to be at least 9 amino acids long, the preferred nucleic acid fragments encoding the immunogenic peptides are at least 27 bases long. Nucleic acid fragments of the invention are also useful as primers for polymerase chain reaction amplification of target DNA and for use as probes in DNA hybridization. In some embodiments a nucleic acid fragment further contains noncontiguous sequence, flanked by contiguous sequence. For example, the fragment can add at least one base, delete at least one base, or change at least one base, and still be useful as a primer or probe. Such methods are well known in the art for the purposes of introducing a restriction endonuclease site to a PCR amplification product, introducing a mutation within a specific sequence, etc.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook et al., Molecular Cloning: A Laboratory Manual (2nd ed., Cold Spring Harbor Laboratory Press, 1989); Anderson et al., Nucleic Acid Hybridisation: A Practical Approach Ch. 4 (IRL Press Limited).

More stringent conditions (such as higher temperature, lower ionic strength, higher formamide, or other denaturing agent) can also be used, although the rate of hybridization will be affected. Other agents can be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridisation: A Practical Approach Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log[Na^+])+0.41(\% G+C)-600/N-0.72(\% \text{ formamide})$$

where N is the length of the duplex formed, [Na$^+$] is the molar concentration of the sodium ion in the hybridization or washing solution, and % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex is able to form with a greater degree of base pair mismatching than could occur under "highly stringent conditions". Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl, e.g., in 6× salt sodium citrate (SSC), for oligonucleotide probes up to about 20 nucleotides is given by:

$$T_m=2°C. \text{ per A-T base pair}+4°C. \text{ per G-C base pair}$$

High stringency washing conditions for oligonucleotides are usually at a temperature of 0-5° C. below the $T_m$ of the oligonucleotide in 6×SSC, 0.1% SDS.

In another embodiment, related nucleic acid molecules comprise or consist of a nucleotide sequence that is at least about 70 percent identical to the nucleotide sequence as shown in either SEQ ID NO:1 or SEQ ID NO:3, or comprise or consist essentially of a nucleotide sequence encoding a polypeptide that is at least about 70 percent identical to the polypeptide as set forth in either SEQ ID NO:2 or SEQ ID NO:4. In certain embodiments, the nucleotide sequences are about 75 percent, or about 80 percent, or about 85 percent, or about 90 percent, or about 95, 96, 97, 98, or 99 percent identical to the nucleotide sequence as shown in either SEQ ID NO:1 or SEQ ID NO:3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in either SEQ ID NO:2 or SEQ ID NO:4. Related nucleic acid molecules encode polypeptides possessing at least one activity of the polypeptide set forth in either SEQ ID NO:2 or SEQ ID NO:4.

Differences in the nucleic acid sequence can result in conservative and/or non-conservative modifications of the amino acid sequence relative to the amino acid sequence of either SEQ ID NO:2 or SEQ ID NO:4. Conservative modifications to the amino acid sequence of either SEQ ID NO:2 or SEQ ID NO:4 (and the corresponding modifications to the encoding nucleotides) will produce a polypeptide having functional and chemical characteristics similar to those of res02 or inv19 polypeptides. In contrast, substantial modifications in the functional and/or chemical characteristics of res02 or inv19 polypeptides can be accomplished by selecting substitutions in the amino acid sequence of either SEQ ID NO:2 or SEQ ID NO:4 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" can involve a substitution of a native amino acid residue with a normative residue such that there is little or no effect on the polarity or charge of the amino acid residue at that position. Furthermore, any native residue in the polypeptide can also be substituted with alanine, as has been previously described for "alanine scanning mutagenesis". Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues can be divided into the following classes based on common side chain properties: (1) hydrophobic: norleucine, Met, Ala, Val, Leu, Ile; (2) neutral hydrophilic: Cys, Ser, Thr; (3) acidic: Asp, Glu; (4) basic: Asn, Gln, His, Lys, Arg; (5) residues that influence chain orientation: Gly, Pro; and (6) aromatic: Trp, Tyr, Phe.

Thus, for example, conservative amino acid substitutions can involve the exchange of a member from one of these classes for another member from the same class. Non-conservative amino acid substitutions can involve the exchange of a member of one of these classes for a member from another class.

In making such changes, the hydropathy index of amino acids can be considered. Each amino acid has been assigned a hydropathy index on the basis of its hydrophobicity and charge characteristics. The hydropathy indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the amino acid hydropathy index in conferring interactive biological function on a protein is generally understood in the art. Kyte J et al. (1982) *J Mol Biol* 157:105-32. It is known that certain amino acids can be substituted for other amino acids having a similar hydropathy index or score and still retain a similar biological activity. In making changes based upon the hydropathy index, the substitution of amino acids whose hydropathy indices are within +2 is preferred, those which are within +1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One can also identify epitopes from primary amino acid sequences on the basis of hydrophilicity. These regions are also referred to as "epitopic core regions".

Desired amino acid substitutions (whether conservative or non-conservative) can be determined by those skilled in the art at the time such substitutions are desired. For example, amino acid substitutions can be used to identify important residues of the res02 or inv19 polypeptide, or to increase or decrease the affinity of the res02 or inv19 polypeptides described herein. Exemplary amino acid substitutions are set forth in Table 2.

TABLE 2

Amino Acid Substitutions.

| ORIGINAL RESIDUES | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in either SEQ ID NO:2 or SEQ ID NO:4 using well-known techniques. For identifying suitable areas of the molecule that can be changed without destroying biological activity, one skilled in the art can target areas not believed to be important for activity. For example, when similar polypeptides with similar activities from the same species or from other species are known, one skilled in the art can compare the amino acid sequence of a res02 or inv19 polypeptide to such similar polypeptides. With such a comparison, one can identify residues and portions of the molecules that are conserved among similar polypeptides. It will be appreciated that changes in areas of the res02 or inv19 molecule that are not conserved relative to such similar polypeptides would be less likely to adversely affect the biological activity and/or structure of a res02 or inv19 polypeptide. One skilled in the art would also know that, even in relatively conserved regions, one can substitute chemically similar amino acids for the naturally occurring residues while retaining activity (conservative amino acid residue substitutions). Therefore, even areas that may be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a res02 or inv19 polypeptide that correspond to amino acid residues that are important for activity or structure in similar polypeptides. One skilled in the art can opt for chemically similar amino acid substitutions for such predicted important amino acid residues of res02 or inv19 polypeptides.

In other embodiments, related nucleic acid molecules comprise or consist of a nucleotide sequence encoding a polypeptide as set forth in either SEQ ID NO:2 or SEQ ID NO:4 with at least one amino acid insertion and wherein the polypeptide has an activity of the polypeptide set forth in either SEQ ID NO:2 or SEQ ID NO:4, or a nucleotide sequence encoding a polypeptide as set forth in either SEQ ID NO:2 or SEQ ID NO:4 with at least one amino acid deletion and wherein the polypeptide has an activity of the polypeptide set forth in either SEQ ID NO:2 or SEQ ID NO:4. Related nucleic acid molecules also comprise or consist of a nucleotide sequence encoding a polypeptide as set forth in either SEQ ID NO:2 or SEQ ID NO:4 wherein the polypeptide has a carboxyl- and/or amino-terminal truncation and further wherein the polypeptide has an activity of the polypeptide set forth in either SEQ ID NO:2 or SEQ ID NO:4. Related nucleic acid molecules also comprise or consist of a nucleotide sequence encoding a polypeptide as set forth in either SEQ ID NO:2 or SEQ ID NO:4 with at least one modification selected from the group consisting of amino acid substitutions, amino acid insertions, amino acid deletions, carboxyl-terminal truncations, and amino-terminal truncations and wherein the polypeptide has an activity of the polypeptide set forth in either SEQ ID NO:2 or SEQ ID NO:4.

In addition, the polypeptide comprising the amino acid sequence of either SEQ ID NO:2 or SEQ ID NO:4, or other res02 or inv19 polypeptide, can be fused to a homologous polypeptide to form a homodimer or to a heterologous polypeptide to form a heterodimer. Heterologous peptides and polypeptides include, but are not limited to: an epitope to allow for the detection and/or isolation of a res02 or inv19 fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in either SEQ ID NO:2 or SEQ ID NO:4, or other res02 or inv19 polypeptide.

Fusions can be made either at the amino-terminus or at the carboxyl-terminus of the polypeptide comprising the amino acid sequence set forth in either SEQ ID NO:2 or SEQ ID NO:4, or other res02 or inv19 polypeptide. Fusions can be direct with no linker or adapter molecule, or they can be through a linker or adapter molecule. A linker or adapter molecule can be one or more amino acid residues, typically from about 20 to about 50 amino acid residues. A linker or adapter molecule can also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of either SEQ ID NO:2 or SEQ ID NO:4, or other res02 or inv19 polypeptide, is fused to one or more domains of an Fc region of human IgG. Antibodies comprise two functionally distinct parts, a variable domain known as "Fab" that binds an antigen, and a constant domain known as "Fc" that is involved in effector functions such as complement activation and attack by phagocytic cells. An Fc has a long serum half-life, whereas an Fab is short-lived. Capon D J et al. (1989) *Nature* 337:525-31. When constructed together with a therapeutic protein, an Fc domain can provide longer half-life or incorporate such functions as Fc receptor binding, protein A binding, complement fixation, and perhaps even placental transfer.

In one example, a human IgG hinge, CH2, and CH3 region can be fused at either the amino-terminus or carboxyl-terminus of the res02 polypeptides using methods known to the skilled artisan. In another example, a human IgG hinge, CH2, and CH3 region can be fused at either the amino-terminus or carboxyl-terminus of a res02 polypeptide fragment.

The resulting fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region can be a naturally occurring Fc region, or it can be altered to improve certain qualities, such as therapeutic qualities, circulation time, or reduced aggregation.

Identity and similarity of related nucleic acid molecules and polypeptides are readily calculated by known methods. Such methods include, but are not limited to those described in Computational Molecular Biology (A. M. Lesk, ed., Oxford University Press 1988); Biocomputing: Informatics and Genome Projects (D. W. Smith, ed., Academic Press 1993); Computer Analysis of Sequence Data (Part 1, A. M. Griffin and H. G. Griffin, eds., Humana Press 1994); G. von Heinle, Sequence Analysis in Molecular Biology (Academic Press 1987); Sequence Analysis Primer (M. Gribskov and J. Devereux, eds., M. Stockton Press 1991); and Carillo et al. (1988) *SIAM J Applied Math* 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux J et al. (1984) *Nucleic Acids Res* 12(1 Pt 1):387-95; Genetics Computer Group, University of Wisconsin, Madison, Wis.), BLASTP, BLASTN, and FASTA (Altschul S F et al. (1990) *J Mol Biol* 215:403-10). The BLASTX program is publicly available from the National Center for Biotechnology Information (NCBI) and other sources (Altschul et al., BLAST Manual (NCB NLM NIH, Bethesda, Md.); Altschul S F et al. (1990) *J Mol Biol* 215:403-10). The well-known Smith Waterman algorithm can also be used to determine identity.

Certain alignment schemes for aligning two amino acid sequences can result in the matching of only a short region of the two sequences, and this small aligned region can have very high sequence identity even though there is no significant relationship between the two full-length sequences. Accordingly, in one embodiment, the selected alignment method (e.g., GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm. See: Dayhoff et al., 5 Atlas of Protein Sequence and Structure (Supp. 3 1978) (PAM250 comparison matrix); Henikoff S et al. (1992) *Proc Natl Acad Sci USA* 89:10915-19 (BLOSUM 62 comparison matrix).

Preferred parameters for polypeptide sequence comparison include the following: Algorithm: Needleman S B et al. (1970) *J Mol Biol* 48:443-53; Comparison matrix: BLOSUM 62 (Henikoff et al, supra); Gap Penalty: 12; Gap Length Penalty: 4; Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following: Algorithm: Needleman et al., supra; Comparison matrix: matches=+10, mismatch=0; Gap Penalty: 50; Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity can be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a res02 or inv19 polypeptide can readily be obtained in a variety of ways including, without limitation, chemical synthesis, genomic library screening, expression library screening, and/or PCR amplification of genomic DNA.

Recombinant DNA methods used herein are generally those set forth in Sambrook et al., Molecular Cloning: A Laboratory Manual (2nd ed., Cold Spring Harbor Laboratory Press, 1989) and/or Current Protocols in Molecular Biology (Ausubel et al., eds., Green Publishers Inc. and Wiley and Sons 1994). The invention provides for nucleic acid molecules as described herein and methods for obtaining such molecules.

Where a gene encoding the amino acid sequence of a res02 or inv19 polypeptide has been identified from one species, all or a portion of that gene can be used as a probe to identify orthologs or related genes from the same species. The probes or primers can be used to screen genomic DNA from various bacteria believed to express the res02 or inv19 polypeptide. In addition, part or all of a nucleic acid molecule having the sequence as set forth in either SEQ ID NO:1 or SEQ ID NO:3 can be used to screen a genomic library to identify and isolate a gene encoding the amino acid sequence of a res02 or inv19 polypeptide. Typically, conditions of moderate or high stringency will be employed for screening to minimize the number of false positives obtained from the screening.

Nucleic acid molecules encoding the amino acid sequence of res02 or inv19 polypeptides can also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below can be followed to produce these polynucleotides and to express the encoded polypeptides. For example, by inserting a nucleic acid sequence that encodes the amino acid sequence of a res02 or inv19 polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a res02 or inv19 polypeptide can be inserted into an expression vector. By introducing the expression vector into an appropriate host, the encoded res02 or inv19 polypeptide can be produced in large amounts.

Another method for obtaining a suitable nucleic acid sequence is the polymerase chain reaction (PCR). In this method, DNA template is prepared from an appropriate source. Two primers, typically complementary to two separate regions of DNA encoding the amino acid sequence of a res02 or inv19 polypeptide, are then added to the template DNA along with a polymerase such as Taq polymerase, and the polymerase amplifies the DNA region between the two primers.

Another means of preparing a nucleic acid molecule encoding the amino acid sequence of a res02 or inv19 polypeptide is chemical synthesis using methods well known to the skilled artisan such as those described by Engels et al. (1989) *Angew Chem Intl Ed* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a res02 or inv19 polypeptide will be several hundred nucleotides in length. Nucleic acids larger than about 100 nucleotides can be synthesized as several fragments using these methods. The fragments can then be ligated together to form the full-length nucleotide sequence of a res02 or inv19 gene. Other methods known to the skilled artisan can be used as well.

In certain embodiments, nucleic acid variants contain codons which have been altered for optimal expression of a res02 or inv19 polypeptide in a given host cell. Particular codon alterations will depend upon the res02 or inv19 polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes can be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

In some cases, it may be desirable to prepare nucleic acid molecules encoding res02 or inv19 polypeptide variants. Nucleic acid molecules encoding variants can be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, can also be used to prepare such variants. Other methods known to the skilled artisan may be used as well.

Vectors and Host Cells

A nucleic acid molecule encoding the amino acid sequence of a res02 or inv19 polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a res02 or inv19 polypeptide can be amplified/expressed in prokaryotic, yeast, insect (baculovirus systems) and/or eukaryotic host cells. Selection of the host cell will depend in part on whether a res02 or inv19 polypeptide is to be post-translationally modified (e.g., glycosylated and/or phosphorylated). If so, yeast, insect, or mammalian host cells are preferable. For a review of expression vectors, see Meth. Enz., vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. For expression of res02 or inv19, expression vectors used in any of the host cells typically will include one or more of the following nucleotide sequences: a promoter, one or more enhancer sequences, an origin of replication, a transcriptional termination sequence, a sequence encoding a leader sequence for polypeptide secretion, a ribosome binding site, a polylinker region for inserting the nucleic acid encoding the polypeptide to be expressed, and a selectable marker element.

Optionally, the vector can contain a "tag"-encoding sequence, i.e., an oligonucleotide molecule located at the 5' or 3' end of the res02 or inv19 polypeptide coding sequence; the oligonucleotide sequence encodes polyHis (such as hexa-His), or another "tag" such as FLAG, HA (hemaglutinin influenza virus), or myc for which commercially available antibodies exist. This tag is typically fused to the polypeptide upon expression of the polypeptide, and can serve as a means for affinity purification of the res02 or inv19 polypeptide from the host cell. Affinity purification can be accomplished, for example, by column chromatography using antibodies against the tag as an affinity matrix. Optionally, the tag can subsequently be removed from the purified res02 or inv19 polypeptide by various means such as using certain peptidases for cleavage.

Flanking sequences can be homologous (i.e., from the same species and/or strain as the host cell), heterologous (i.e., from a species other than the host cell species or strain), hybrid (i.e., a combination of flanking sequences from more than one source), or synthetic, or the flanking sequences can be native sequences which normally function to regulate res02 or inv19 polypeptide expression. As such, the source of a flanking sequence can be any prokaryotic or eukaryotic organism, any vertebrate or invertebrate organism, or any plant, provided that the flanking sequence is functional in, and can be activated by, the host cell machinery.

Flanking sequences useful in the vectors of this invention can be obtained by any of several methods well known in the art. Typically, flanking sequences useful herein, other than the res02 or inv19 gene flanking sequences, will have been previously identified by mapping and/or by restriction endonuclease digestion and can thus be isolated from the proper source using the appropriate restriction endonucleases. In some cases, the full nucleotide sequence of a flanking sequence may be known. Here, the flanking sequence can be synthesized using the methods described herein for nucleic acid synthesis or cloning.

Where all or only a portion of the flanking sequence is known, it can be obtained using PCR and/or by screening a genomic library with a suitable oligonucleotide and/or flanking sequence fragment from the same or another species. Where the flanking sequence is not known, a fragment of DNA containing a flanking sequence can be isolated from a larger piece of DNA that may contain, for example, a coding sequence or even another gene or genes. Isolation can be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a res02 or inv19 polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. A neomycin resistance gene can also be used for selection in prokaryotic and eukaryotic host cells.

Other selection genes can be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a res02 or inv19 polypeptide. As a result, increased quantities of res02 or inv19 polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a res02 or inv19 polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence can be used to direct a res02 or inv19 polypeptide out of the host cell. Typically, a nucleotide sequence encoding the signal sequence is positioned in the coding region of a res02 or inv19 nucleic acid molecule, or directly at the 5' end of a res02 or inv19 polypeptide coding region. Many signal sequences have been identified, and any of those that are functional in the selected host cell can be used in conjunction with a res02 or inv19 nucleic acid molecule. Additionally, a signal sequence can be chemically synthesized using methods described herein. In most cases, the secretion of a res02 or inv19 polypeptide from the host cell via the presence of a signal peptide will result in the removal of the signal peptide from the secreted res02 or inv19 polypeptide. The signal sequence can be a component of the vector, or it can be a part of a res02 or inv19 nucleic acid molecule that is inserted into the vector.

Included within the scope of this invention is the use of either a nucleotide sequence encoding a native res02 or inv19 polypeptide without a signal sequence or a nucleotide sequence encoding a heterologous signal sequence joined to a res02 or inv19 polypeptide coding region. The heterologous signal sequence selected should be one that is recognized and processed, i.e., cleaved by a signal peptidase, by the host cell. For prokaryotic host cells, the signal sequence is provided by a prokaryotic signal sequence selected, for example, from the group of the alkaline phosphatase, penicillinase, or heat-stable enterotoxin II leaders. For yeast secretion, the signal sequence can be provided by the yeast invertase, alpha factor, or acid phosphatase leaders. In mammalian cell expression any suitable mammalian signal sequence can be employed.

In some cases, such as where glycosylation is desired in a eukaryotic host cell expression system, one can manipulate the various presequences to improve glycosylation or yield. For example, one can alter the peptidase cleavage site of a particular signal peptide, or add pro-sequences, which also can affect glycosylation. The final protein product can have, in the −1 position (relative to the first amino acid of the mature protein) one or more additional amino acids incident to expression, which may not have been totally removed. For example, the final protein product can have one or two amino acid residues found in the peptidase cleavage site, attached to the amino-terminus. Alternatively, use of some enzyme cleavage sites may result in a slightly truncated form of the desired res02 or inv19 polypeptide, if the enzyme cuts at such area within the mature polypeptide.

The expression and cloning vectors of the present invention will typically contain a promoter that is recognized by the host organism and operably linked to the molecule encoding the res02 or inv19 polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding res02 or inv19 polypeptide by removing the promoter from the source DNA by restriction enzyme digestion and inserting the desired promoter sequence into the vector. The native res02 or inv19 promoter sequence can be used to direct amplification and/or expression of a res02 or inv19 nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus (CMV), retroviruses, hepatitis-B virus and Simian Virus 40 (SV40). Other suitable mammalian promoters include heterologous mammalian promoters, for example, heat-shock promoters and the actin promoter.

Additional promoters which may be of interest in controlling res02 or inv19 gene expression include, but are not limited to: the SV40 early promoter region (Benoist C et al. (1981) *Nature* 290:304-10); the CMV promoter; the promoter contained in the 3' long terminal repeat of Rous sarcoma virus (Yamamoto T et al. (1980) *Cell* 22:787-97); the herpes thymidine kinase promoter (Wagner M J et al. (1981) *Proc Natl Acad Sci USA* 78:1441-45); the regulatory sequences of the metallothionine gene (Brinster R L et al. (1982) *Nature* 296:39-42); prokaryotic expression vectors such as the beta-lactamase promoter (Villa-Kamaroff et al. (1978) *Proc Natl Acad Sci USA* 75:3727-31); or the tac promoter (DeBoer et al. (1983) *Proc Natl Acad Sci USA* 80:21-25). Also of interest are the following animal transcriptional control regions, which exhibit tissue specificity and have been utilized in transgenic animals: the elastase I gene control region which is active in pancreatic acinar cells (Swift et al. (1984) *Cell* 38:639-46; Omitz et al. (1986) *Cold Spring Harbor Symp Quant Biol* 50:399-409; MacDonald (1987) *Hepatology* 7:425-515); the insulin gene control region which is active in pancreatic beta cells (Hanahan (1985) *Nature* 315:115-22); the immunoglobulin gene control region which is active in lymphoid cells (Grosschedl R et al. (1984) *Cell* 38:647-58; Adams J M et al. (1985) *Nature* 318:533-38; Alexander W S et al. (1987) *Mol Cell Biol* 7:1436-44); the mouse mammary tumor virus control region which is active in testicular, breast, lymphoid and mast cells (Leder P et al. (1986) *Cell* 45:485-95); the albumin gene control region which is active in liver (Pinkert Calif. et al. (1987) *Genes Dev* 1:268-76); the alpha-fetoprotein gene control region which is active in liver (Krumlauf R et al. (1985) *Mol Cell Biol* 5:1639-48; Hammer R E et al. (1987) *Science* 235:53-58); the alpha 1-antitrypsin gene control region which is active in the liver (Kelsey G D et al. (1987) *Genes Dev* 1:161-71); the beta-globin gene control region which is active in myeloid cells (Magram J et al. (1985) *Nature* 315:338-40; Kollias G et al. (1986) *Cell* 46:89-94); the myelin basic protein gene control region which is active in oligodendrocyte cells in the brain (Readhead C et al. (1987) *Cell* 48:703-12); the myosin light chain-2 gene control region which is active in skeletal muscle (Shani M (1985) *Nature* 314:283-86); and the gonadotropic releasing hormone gene control region which is active in the hypothalamus (Mason A J et al. (1986) *Science* 234:1372-78).

An enhancer sequence can be inserted into the vector to increase the transcription of a DNA encoding a res02 or inv19 polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer can be spliced into the vector at a position 5' or 3' to a res02 or inv19 nucleic acid molecule, it is typically located at a site 5' from the promoter.

Expression vectors of the invention can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP—N2 (Clontech, Palo Alto, Calif.), pETL (BlueBacli, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla, Calif.), PCR cloning plasmids designed for cloning Taq-amplified PCR products (e.g., TOPO™ TA Cloning® Kit, PCR2.1™ plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding a res02 or inv19 polypeptide has been inserted into the proper site of the vector, the completed vector can be inserted into a suitable host cell for amplification and/or polypeptide expression. The transformation of an expression vector for a res02 or inv19 polypeptide into a selected host cell can be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells can be prokaryotic host cells (such as *E. coli*) or eukaryotic host cells (such as a yeast, insect, or vertebrate cell). The host cell, when cultured under appropriate conditions, synthesizes a res02 or inv19 polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(–) cells (Urlaub G et al. (1980) *Proc Natl Acad Sci USA* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, BALB/c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like can also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems can be utilized in the methods of the present invention. Such systems are described, for example, in Kitts P A et al. (1993) *Biotechniques* 14:810-17; Lucklow V A (1993) *Curr Opin Biotechnol* 4:564-72; and Lucklow V A et al. (1993) *J Virol* 67:4566-79. Preferred insect cells are Sf-9 and Hi5 (Invitrogen).

One can also use transgenic animals to express glycosylated res02 or inv19 polypeptides. For example, one can use a transgenic milk-producing animal (a cow or goat, for example) and obtain the present glycosylated polypeptide in the animal milk. One can also use plants to produce res02 or inv19 polypeptides, however, in general, the glycosylation occurring in plants is different from that produced in mammalian cells, and can result in a glycosylated product which is not suitable for human therapeutic use.

Polypeptide Production

Host cells comprising a res02 or inv19 polypeptide expression vector can be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which can be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a res02 or inv19 polypeptide produced by a host cell can be evaluated using standard methods known in the art. Such methods include, without limitation, Western immunoblot analysis, SDS-polyacrylamide gel electrophoresis, non-denaturing gel electrophoresis, high performance liquid chromatography (HPLC) separation, immunoprecipitation, and/or activity assays such as DNA binding gel shift assays.

If a res02 or inv19 polypeptide has been designed to be secreted from the host cells, the majority of polypeptide may be found in the cell culture medium. If, however, the res02 or inv19 polypeptide is not secreted from the host cells, it will be present in the cytoplasm and/or the nucleus (for eukaryotic host cells) or in the cytosol (for bacterial host cells).

For a res02 or inv19 polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a res02 or inv19 polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized res02 or inv19 polypeptide can then be analyzed using gel electrophoresis, immunoprecipitation, or the like. If it is desired to isolate the res02 or inv19 polypeptide, isolation can be accomplished using standard methods such as those described herein and in Marston F A et al. (1990) *Methods Enzymol* 182:264-76.

In some cases, a res02 or inv19 polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol (DTT)/dithiane DTT, and 2-2-mercaptoethanol (βME)/dithio-β(ME). In many instances, a cosolvent can be used or can be needed to increase the efficiency of the refolding, and the more common reagents used for this purpose include glycerol, polyethylene glycol of various molecular weights, arginine and the like.

If inclusion bodies are not formed to a significant degree upon expression of a res02 or inv19 polypeptide, then the polypeptide will be found primarily in the supernatant after centrifugation of the cell homogenate. The polypeptide can be further isolated from the supernatant using methods such as those described herein.

The purification of a res02 or inv19 polypeptide from solution can be accomplished using a variety of techniques. If the polypeptide has been synthesized such that it contains a tag such as Hexahistidine (res02 or inv19 polypeptide/hexaHis) or other small peptide such as FLAG (Eastman Kodak Co., New Haven, Conn.) or myc (Invitrogen, Carlsbad, Calif.) at either its carboxyl- or amino-terminus, it can be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of res02 or inv19 polypeptide/polyHis. See, e.g., Current Protocols in Molecular Biology 10.11.8 (Ausubel et al., eds., Green Publishers, Inc. and Wiley and Sons, 1993).

Additionally, res02 or inv19 polypeptides can be purified through the use of a monoclonal antibody that is capable of specifically recognizing and binding to a res02 or inv19 polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques can be combined to achieve increased purity.

Res02 or inv19 polypeptides can also be prepared by chemical synthesis methods (such as solid phase peptide synthesis) using techniques known in the art such as those set forth by Merrifield et al. (1963) *J Am Chem Soc* 85:2149; Houghten R A et al. (1985) *Proc Natl Acad Sci USA* 82:5131-35; and Stewart and Young, Solid Phase Peptide Synthesis (Pierce Chemical Co., 1984). Such polypeptides can be synthesized with or without a methionine on the amino-terminus. Chemically synthesized res02 or inv19 polypeptides can be oxidized using methods set forth in these references to form disulfide bridges. Chemically synthesized res02 or inv19 polypeptides are expected to have comparable biological activity to the corresponding res02 or inv19 polypeptides produced recombinantly or purified from natural sources, and thus can be used interchangeably with a recombinant or natural res02 or inv19 polypeptide.

Another means of obtaining res02 or inv19 polypeptide is via purification from biological samples such as capsular polysaccharide-expressing bacterial cells in which the res02 or inv19 polypeptide is naturally found. Such purification can be conducted using methods for protein purification as described herein. The presence of the res02 or inv19 polypeptide during purification can be monitored, for example, using an antibody prepared against recombinantly produced res02 or inv19 polypeptide or peptide fragments thereof.

A number of additional methods for producing nucleic acids and polypeptides are known in the art, and the methods can be used to produce polypeptides having specificity for res02 or inv19 polypeptide. See, e.g., Roberts R W et al. (1997) *Proc Natl Acad Sci USA* 94:12297-302, which describes the production of fusion proteins between an mRNA and its encoded peptide. See also, Roberts R W (1999) *Curr Opin Chem Biol* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive res02 or inv19 polypeptide expression libraries, which can subsequently be used for high throughput phenotypic screening in a variety of assays, such as biochemical assays, cellular assays, and whole organism assays (e.g., plant, mouse, etc.).

Selective Binding Agents

The term "selective binding agent" refers to a molecule that has specificity for one or more antigens selected from res02 polypeptide, inv19 polypeptide, PSA, PSB, PSC, PSD, PSE, PSF, PSG, PSH, and fragments thereof. Suitable selective binding agents include, but are not limited to, antibodies and derivatives thereof, polypeptides, and small molecules. Suitable selective binding agents can be prepared using methods known in the art.

Selective binding agents such as antibodies and antibody fragments that bind res02 polypeptide, inv19 polypeptide, PSA, PSB, PSC, PSD, PSE, PSF, PSG, PSH, and fragments thereof, are within the scope of the present invention. The antibodies can be polyclonal including monospecific polyclonal; monoclonal (MAbs); recombinant; chimeric; humanized, such as CDR-grafted; human; single chain; and/or bispecific; as well as fragments, variants, or derivatives thereof. Antibody fragments include those portions of the antibody that bind to an epitope of an antigen. Examples of such fragments include Fab, F(ab') and F(ab')$_2$ fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an antigen generally are produced in animals (e.g., rabbits or mice) by means of multiple subcutaneous or intraperitoneal injections of antigen and an adjuvant. It may be useful to conjugate an antigen to a carrier protein that is immunogenic in the species to be immunized, such as keyhole limpet hemocyanin, albumin, bovine thyroglobulin, or soybean trypsin inhibitor. Also, aggregating agents such as alum are used to enhance the immune response. After immunization, the animals are bled and the serum is assayed for antigen-specific antibody titer.

Monoclonal antibodies directed toward an antigen are produced using any method that provides for the production of antibody molecules by continuous cell lines in culture. Examples of suitable methods for preparing monoclonal antibodies include the hybridoma methods of Kohler G et al. (1975) *Nature* 256:495-97 and the human B-cell hybridoma method (Kozbor D et al. (1984) *J Immunol* 133:3001-5; Brodeur et al., Monoclonal Antibody Production Techniques and Applications 51-63 (Marcel Dekker, Inc., 1987). Also provided by the invention are hybridoma cell lines that produce monoclonal antibodies reactive with res02 polypeptide, inv19 polypeptide, PSA, PSB, PSC, PSD, PSE, PSF, PSG, PSH, and fragments thereof.

The antibodies of the invention can be employed in any known assay method, such as competitive binding assays, direct and indirect sandwich assays, Western immunoblot assays, and immunoprecipitation assays (Sola, Monoclonal Antibodies: A Manual of Techniques, CRC Press, Inc., 1987, pp. 147-158) for the detection and quantitation of antigen. The antibodies will bind antigen with an affinity that is appropriate for the assay method being employed.

For diagnostic applications, in certain embodiments, anti-res02, or anti-inv19, or anti-capsular polysaccharide antibodies can be labeled with a detectable moiety. The detectable moiety can be any one that is capable of producing, either directly or indirectly, a detectable signal. For example, the detectable moiety can be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, beta-galactosidase, or horseradish peroxidase (Bayer E A et al. (1990) *Methods Enzymol* 184:138-60).

Competitive binding assays rely on the ability of a labeled standard (e.g., a res02 or inv19 polypeptide, a capsular polysaccharide, or an immunologically reactive portion thereof) to compete with the test sample analyte (a res02 or inv19 polypeptide or a capsular polysaccharide) for binding with a limited amount of anti-res02, anti-inv19, or anti-capsular polysaccharide antibody. The amount of an antigen in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody can itself be labeled with a detectable moiety (direct sandwich assays) or can be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

EXAMPLES

The following examples are illustrative only and are not intended to limit the scope of the invention in any way.

Example 1

Bacterial Strain and Isolation of *B. Fragilis* Polysaccharide

*B. fragilis* NCTC9343 was originally obtained from the National Collection of Type Cultures (London, England), stored at −80° F. in yeast both until used, and grown anaerobically as previously described. Pantosti A et al. (1991) *Infect Immun* 59:2075-2082. The capsular polysaccharide from *B. fragilis* NCTC9343 was isolated by hot phenol/water extraction and subsequent purification of PSA and PSB performed as previously described. Tzianabos A et al. (1992) *J Biol Chem* 267:18230-18235.

Example 2

Identification of Res02 and Inv19

Hypothesizing that the DNA inversions of the seven promoter regions would be controlled by specific proteins that are involved in recombining DNA, a search of *B. fragilis* NCTC9343 genomic sequences provided by the microbial pathogen group at the Sanger Centre was performed, looking for open reading frames (ORFs) with homology to fimB and fimE, two genes of *E. coli* that are involved in inverting DNA. Five ORFs were retrieved. These five *B. fragilis* ORFs were then used to reprobe the database, and twenty-five homologs were retrieved and given temporary designations of inv1-inv25. Three additional homologs have subsequently been retrieved and given temporary designations of inv26-inv28.

Based on our data, we knew that the gene product that is involved in inverting the polysaccharide promoters would be conserved in all strains. Therefore, DNA hybridizations were performed to probe a collection of *B. fragilis* strains with internal portions of each of these 25 ORFs.

Seven of the original twenty-five ORFs (and nine of the twenty-eight ORFs) were found to be conserved within *B. fragilis*. Analysis of the sequence surrounding one of these conserved genes, inv19, demonstrated a divergently transcribed gene of the serine site-specific recombinase family which was designated res02 (now also denoted mpi) and was also shown by hybridization to be conserved among *B. fragilis*.

Fifteen out of fifteen *B. fragilis* strains tested probed positive with internal portion of res02 (Table 3). Twenty-five out of twenty-six *B. fragilis* strains tested probed positive with internal portion of inv19; the one negative strain was 1279155I (Table 4).

TABLE 3 res02 probe-positive *B. fragilis* strains.

| 1279-2 | 45703 | CM3 |
|---|---|---|
| 13141 | B110 | CM11 |
| 17905 | B117 | CM12 |
| 2429 | B124 | PA5 |
| 26877 | B272 | US398 |

TABLE 4 inv19 probe-positive *B. fragilis* strains.

| 12775L1II | 1285531I | 2429 | B117 | CM11 |
|---|---|---|---|---|
| 1277810I | 1287245I | 17905 | B124 | CM12 |
| 1279-2 | 12905-23V | 26877 | B272 | IL89375II |
| 1281262I | 1291662III | 45703 | B356772I | PA5 |
| 1284-2 | 13141 | B110 | CM33 | US398 |

Several of these conserved genes were cloned into a vector along with the PSA promoter invertible region and analyzed for their ability to invert the PSA promoter region. Res02 was demonstrated to bring about inversion of the PSA promoter region.

Example 3

Method of Deleting Res02 from the *b. Fragilis* 9343 Chromosome

In order to delete the res02 gene from the *B. fragilis* 9343 chromosome, homologous recombination with a double crossover event was employed to replace the full length copy of res02 with a deleted copy. To do this, plasmid pKGW10 was created. In order to construct this plasmid, 9343 chromosomal DNA was used as a template to amplify the DNA flanking the region to be deleted (FIG. 5). Primer pairs inv19D-1 plus inv19D-2 and inv19D-5 plus inv19D-6 were used in two separate PCRs. Table 5 shows that primers inv19D-1 and inv19D-6 each incorporate a BamHI restriction endonuclease site (shown underlined), while primers inv19D-2 and inv19D-6 each incorporate an NcoI restriction endonuclease site (shown underlined).

TABLE 5

Sequences of the primers used to make the res02 deletion.

| | |
|---|---|
| inv19-D1 → | 5'-cc<u>ggatcc</u>agtactgataact (SEQ ID NO:11) ccggtgactcc-3' |
| inv19-D2 ← | 5'-at<u>ccatgg</u>ccggtttatgaaa (SEQ ID NO:12) acgatgtatta-3' |
| inv19-D5 → | 5'-cg<u>ccatgg</u>ttttccgtactta (SEQ ID NO:13) ctctcaaataagc-3' |
| inv19-D6 ← | 5'-ggg<u>gatcc</u>atgacatagataa (SEQ ID NO:14) tggggaagagg-3' |

Upon amplification, the resulting amplification products were: Left Flank, inv19-D1→through←inv19-D2, 1,958 bp (FIG. 6, SEQ ID NO:5); and Right Flank, inv19-D5→through←inv19-D6, 2,540 bp (FIG. 7, SEQ ID NO:6).

These primers were placed so that 534 bp of the 594 bp res02 open reading frame were deleted. The resulting PCR products were digested with BamHI and NcoI (restriction sites constructed into the primers) and ligated in a three-way reaction with a *B. fragilis* suicide vector that encoded for erythromycin resistance. This ligation mixture was transformed into *E. coli* and the transformants were tested by both PCR and plasmid digestion for the correct ligation of the flanks. The plasmid containing the correct ligation of the flanks was named pKGW10.

pKGW10 was conjugally transferred from *E. coli* to *B. fragilis* 9343 and the cointegrate (containing all of the DNA of pKGW10 integrated into the chromosome) resulting from homologous recombination was selected by erythromycin resistance (encoded by pKGW10). The cointegrate was passaged in nonselective medium to allow for resolution of the cointegrate by the second recombination event (where either the mutant copy or the wild type copy of res02 was lost along with the intervening plasmid). Bacteria were plated onto medium without antibiotics (approximately 200 colonies per plate). The colonies were replica plated to medium containing erythromycin and the erythromycin-sensitive ($Em^s$) colonies were selected (these $Em^s$ colonies represent those that only have the mutant or wild type copy of res02, but not both). These colonies were screened by PCR for those containing the mutant genotype. PCR was used to determine that each of the seven polysaccharide invertible promoter regions was locked and unable to invert in each of the res02 mutants. Deletion was also confirmed by Southern blot in each case.

Example 4

Monospecific Antisera for PSA-PSH

Monospecific antisera for each of the eight known capsular polysaccharides of *B. fragilis* were prepared as previously described. Comstock L E et al. (1999) *Infect Immun* 67:3525-32; Coyne M J et al. (2000) *Infect Immun* 68:6176-81; Coyne M et al. (2001) *Infect Immun* 69:4342-50; Krinos C M et al. (2001) *Nature* 414:555-8. These monospecific antisera were used in Western immunoblot phenotype analyses of res02 mutants.

Example 5

Deletion of Res02 Locks Capsular Polysaccharide Promoters On or Off

The res02 open reading frame was deleted from the 9343 chromosome by double crossover allelic exchange, resulting in several mutants that all had a chromosomal deletion of res02. Analysis of these mutants demonstrated that each of the seven polysaccharide promoter inversion regions was locked in a single orientation, demonstrating that the Res02 product is involved in the DNA inversions.

Several of these mutants had the PSA and PSE promoter regions locked on and the promoter regions for PSB, PSD, PSF, PSG, and PSH locked off. Therefore, it was expected that this strain would constitutively express PSA, PSC (the promoter of PSC does not undergo inversions) and PSE, but not express PSB, PSD, PSF, PSG, or PSH.

Figure 8:
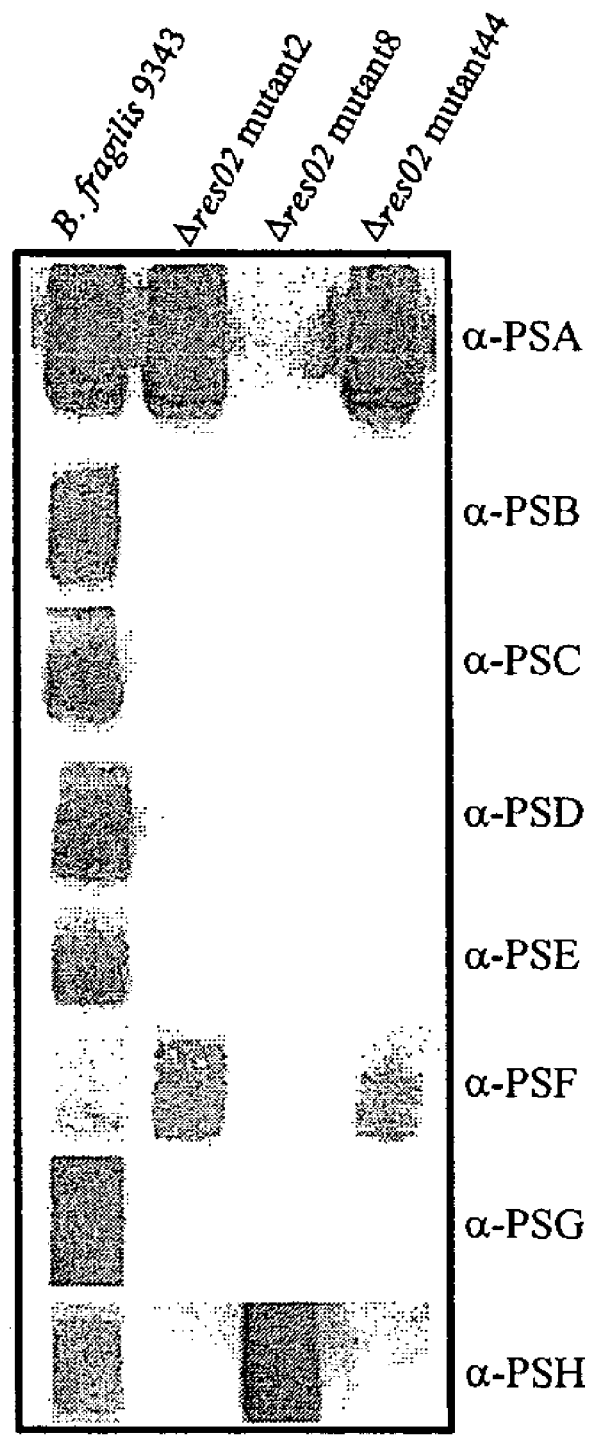
FIG. 8 is a composite of Western immunoblot images demonstrating that mut2 (lane 2) and mut44 (lane 4) express PSA, but not PSB, PSC, PSD, PSE, PSG, or PSH. Small amounts of PSF were expressed by each of these mutant strains, but not by another res02 mutant, res02mut8. Wild-type (lane 1) and res02mut8 (lane 3) are also shown for comparison.

FIG. 8 shows the results of phenotypic analysis of one of these mutants, 9343res02mut44 (mut44). This analysis demonstrated that mut44 indeed synthesized PSA in high quantities (as least ten times more purified PSA is isolated compared to a typical grow-up with wild-type). It was also shown that mut44 was unable to produce six of the other seven capsular polysaccharides, including PSC and PSE (as determined by Western blot analysis, immunoelectrophoresis, and analysis of purified capsular polysaccharide). It was unexpectedly found that, despite the fact that the promoter for the polysaccharide biosynthesis locus of PSF was turned off, mut44 expressed small amounts of PSF (FIG. 8). This observation could be consistent with the existence of a secondary promoter that is unaffected by DNA inversions. However, another mutant, mut8, was discovered to express only PSH and no PSF (FIG. 8). The small amount of PSF expressed by mut 44 does not significantly interfere with the purification of PSA from this strain.

Another res02 mutant, 9343res02mut2 (mut2), was isolated that also had all of the polysaccharide promoter flip regions locked off except for the PSA promoter region, which was locked on. The phenotype of this mutant was found to be the same as mut44, i.e., found to overexpress PSA and to express small amounts of PSF, but none of the other seven known capsular polysaccharides PSB-PSH.

Example 6

Mut44 Overexpresses PSA

By deletion of the open reading frame designated res02, *B. fragilis* strains have been created that overexpress PSA compared to wild type and that are devoid of most or all the other seven known capsular polysaccharide of this strain. These strains make a sufficient amount of PSA to be easily purified to make them attractive for large scale purification of the potent zwitterionic polysaccharide, PSA, for commercial interests.

The yield of total capsular polysaccharide (all eight polysaccharides together) isolated from wild type *B. fragilis* NCTC9343 ranges from 6.26-21.9 mg/liter of culture. After extensive methods for purification of PSA from the other polysaccharides, the yield of pure PSA isolated from wild type *B. fragilis* NCTC9343 ranges from 0-3.1 mg/liter of culture, with an average of 1.56 mg/liter of culture. In the first large grow-up (16 liters) of mut44 there was a yield of 21.8 mg pure PSA per liter of culture. Not only was the yield 14 times greater than from wild type, but the extraction and purification methods were much easier because the PSA did not have to be isolated from the other capsular polysaccharides. Unlike wild type, the yield of PSA from this mutant is expected to be consistently high since expression of PSA is no longer undergoing phase variation due to the promoter being unable to flip off.

Example 7

Large Scale Purification of PSA from Mut44

A 16 liter batch fermentation of mut44 was grown in supplemented basal medium. Following overnight growth, the bacteria were pelleted and resuspended in 667 ml of $dH_2O$ at 68° C. Glass beads were added to the resuspended pellet and placed in a 4 liter water bath. 667 ml of 75% phenol (prewarmed to 68° C.) was added to the mixture and stirred for at least 30 min. The mixture was then stirred overnight in the cold room. The mixture was then centrifuged at 8000 rpm for 20 min. The top aqueous phase was removed (approx. 500 ml) and added to 500 ml of ether in a separatory funnel. The mixture was shaken and allowed to separate for 20 min. The bottom phase was retained. The sample was placed in a rotary evaporator in a 60° C. waterbath for ether evaporation and sample concentration. The sample was placed in dialysis tubing and dialyzed against 10 liters of water with six changes of buffer. 1M Tris was added to make it 6.5% of the volume. $MgCl_2$ and $CaCl_2$ were added to a final concentration of 20 mM. RNase was added to bring the concentration to 3.33 mg/ml and DNase was added to 0.07 mg/ml. The sample was digested overnight at 37° C. The pH of the sample was adjusted to 7.5 with 10M NaOH. Pronase was added to 0.33 mg/ml and incubated overnight. Fresh pronase was added and incubated for an additional 2 hours. EDTA was added to make the solution 50 mM and mixed for 30 min. The sample was precipitated using 5 volumes of −20° C. ethanol. The sample was resuspended in 3% deoxycholate and applied to a sepharose 400 column. Column fractions were monitored by silver-stained SDS-PAGE for separation of high molecular weight capsular polysaccharide and low molecular weight LPS. PSA purity was tested by immunoelectrophoresis and NMR analysis.

Example 8

Deletion of Inv19

The inv19 open reading frame was deleted from the 9343 chromosome by double crossover allelic exchange, resulting in several mutants that all have a chromosomal deletion of inv19.

Biological Deposit

A deposit of mut44 was made with American Type Culture Collection, Manassas, Va. on Mar. 11, 2002, under the description *Bacteroides fragilis:* 9343res02mut44, and assigned to Patent Deposit Designation PTA-4135.

A deposit of mut2 was made with American Type Culture Collection, Manassas, Va. on Oct. 11, 2006, under the description *Bacteroides fragilis:* 9343res02mut2, and assigned to Patent Deposit Designation PTA-7917.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. An isolated *Bacteroides fragilis* (*B. fragilis*) cell producing a native capsular polysaccharide selected from the group consisting of: polysaccharide A (PSA), polysaccharide B (PSB), polysaccharide D (PSD), polysaccharide E (PSE), polysaccharide F (PSF), polysaccharide G (PSG), and polysaccharide H (PSH),
   wherein the promoter controlling expression of the native biosynthetic genes of the native capsular polysaccharide is locked on,
   wherein the promoter is locked on by disabling expression of the endogenous res02 (multiple promoter invertase) gene, said gene comprising the nucleotide sequence of SEQ ID NO:1,
   wherein res02 expression is disabled such that the level of res02 polypeptide is insufficient for inverting the promoter of the native biosynthetic genes of said native capsular polysaccharide, wherein the res02 polypeptide comprises the amino acid sequence of SEQ ID NO:2, and
   wherein the res02 expression is disabled by res02 antisense nucleic acid.

2. The cell according to claim 1, wherein the native capsular polysaccharide is PSA.

3. The cell according to claim 2, wherein the promoters controlling expression of PSB, PSD, PSE, PSF, PSG, and PSH are locked off.

4. The cell according to claim 1, wherein the cell is *B. fragilis* NCTC9343.

5. The cell according to claim 2, wherein the cell is *B. fragilis* NCTC9343.

6. The cell according to claim 3, wherein the cell is *B. fragilis* NCTC9343.

* * * * *

SEQUENCE LISTING

<160> NUMBER OF SEQ ID NOS: 14

<210> SEQ ID NO 1
<211> LENGTH: 594
<212> TYPE: DNA
<213> ORGANISM: Bacteroides fragilis

<400> SEQUENCE: 1

```
atggtaatag cttatttgag agtaagtacg gaaaaacagt ttttggctaa tcagaaggaa      60
gagattatgc gatttgcaga gaagaatggg ttgtcgattg acaagtggta cacagagacc     120
gtaagcggaa gcgtgagcac aaaagacaga aagctatcag agttattgaa gagaatgcat     180 cccgggata cactgattgt aacggagatt tcgagattga gccgtacact gctcgagatt      240
atgactatcc tgaatttttg tattaagaag caggtagtgc tctatagcac caagagggc      300 tatgtgtttc aggacgacat caacagcaag gtgctgggat tcgcgttcgg actgatggcg     360
gaaatagaaa ggaacctgat ttcgatgcgt accaaagaag ctctcgcacg cagaaagcag     420
gaaggaatga ctttaggccg aaagaaaggg gatacgccta aaataaaatt gctgcgtgcc     480
aataagcgcg tacttaccaa agaacttgac aaaggaacta cttactcgga attggcggag     540
aagatggggg tatccagaac aaccctgttc cggtttatga aaacgatgta ttag          594
```

<210> SEQ ID NO 2
<211> LENGTH: 197
<212> TYPE: PRT
<213> ORGANISM: Bacteroides fragilis

<400> SEQUENCE: 2

```
Met Val Ile Ala Tyr Leu Arg Val Ser Thr Glu Lys Gln Phe Leu Ala
1               5                   10                  15
```

```
Asn Gln Lys Glu Glu Ile Met Arg Phe Ala Glu Lys Asn Gly Leu Ser
         20                  25                  30

Ile Asp Lys Trp Tyr Thr Glu Thr Val Ser Gly Ser Val Ser Thr Lys
 35                  40                  45

Asp Arg Lys Leu Ser Glu Leu Leu Lys Arg Met His Pro Gly Asp Thr
 50                  55                  60

Leu Ile Val Thr Glu Ile Ser Arg Leu Ser Arg Thr Leu Leu Glu Ile
 65                  70                  75                  80

Met Thr Ile Leu Asn Phe Cys Ile Lys Lys Gln Val Val Leu Tyr Ser
                 85                  90                  95

Thr Lys Glu Gly Tyr Val Phe Gln Asp Asp Ile Asn Ser Lys Val Leu
                100                 105                 110

Gly Phe Ala Phe Gly Leu Met Ala Glu Ile Glu Arg Asn Leu Ile Ser
                115                 120                 125

Met Arg Thr Lys Glu Ala Leu Ala Arg Arg Lys Gln Glu Gly Met Thr
130                 135                 140

Leu Gly Arg Lys Lys Gly Asp Thr Pro Lys Ile Lys Leu Leu Arg Ala
145                 150                 155                 160

Asn Lys Arg Val Leu Thr Lys Glu Leu Asp Lys Gly Thr Thr Tyr Ser
                165                 170                 175

Glu Leu Ala Glu Lys Met Gly Val Ser Arg Thr Thr Leu Phe Arg Phe
                180                 185                 190

Met Lys Thr Met Tyr
            195

<210> SEQ ID NO 3
<211> LENGTH: 921
<212> TYPE: DNA
<213> ORGANISM: Bacteroides fragilis

<400> SEQUENCE: 3
atggaaatag aaaaattcat taaatctttta gcaagaaaag cgaagttagg cgggcgttac        60
agcacagcca atacctacct ctacactttg cacagttttc agaagtttgc gggaaaagcc       120
tcactgactt ttgaagagat cactcccgag agtatcaagg agtacgagca atacttaatc       180
ctcaacggga acggtacaa cacgatctcg ctctacatgc gcatgttgcg ttccatctgc        240
aatcaggcat cggagcagaa catagcttcg ctcaacaccc gcgagctgtt tgagaatgtt       300
tttatcggca cgaacccac tgccaagcgt gccatctcac ccgtcctcat ttcccgcctg        360
ctcgaagcag atttcagcaa gaacagccgg ctcgattttg cccgcgacct cttcttgcta       420
agcttctacc tgaggggaat cccgtttgtc gacctggtac atctccgcaa gaccgatgtg       480
cagggaaaca tgctcgtttta ttttccgccag aaaacgggac agcaacttac ggtaatcata   540
gaaaactgcg ccaaagtgat cttgcgtaag tatgcctcgc tttgcaaaga atccgtctat       600
ctgctgcccg tcatcagcgc agccggagag gaggggcaca agcagtaccg aagtgcattg       660
agggtataca caaacgcct caaccagata tccggaatac tgaaattgaa gactccgctg        720
acctcttatg tggcacgcca cagttgggcg accacggccc tgcagaaagg ggttccggtt       780
tcagtgatca gtgcaggaat ggggcatgct tcagagaagg tgacatacat ttatctggca       840
tcttttgata caaaacgct cagtaacgca aataaaaaag tgattgccgc cgtgagattt       900
aagaaagagg aggaggagtg a                                                 921

<210> SEQ ID NO 4
<211> LENGTH: 306
```

<212> TYPE: PRT
<213> ORGANISM: Bacteroides fragilis

<400> SEQUENCE: 4

```
Met Glu Ile Glu Lys Phe Ile Lys Ser Leu Ala Arg Lys Ala Lys Leu
1               5                   10                  15

Gly Gly Arg Tyr Ser Thr Ala Asn Thr Tyr Leu Tyr Thr Leu His Ser
            20                  25                  30

Phe Gln Lys Phe Ala Gly Lys Ala Ser Leu Thr Phe Glu Glu Ile Thr
        35                  40                  45

Pro Glu Ser Ile Lys Glu Tyr Glu Gln Tyr Leu Ile Leu Asn Gly Lys
    50                  55                  60

Arg Tyr Asn Thr Ile Ser Leu Tyr Met Arg Met Leu Arg Ser Ile Cys
65                  70                  75                  80

Asn Gln Ala Ser Glu Gln Asn Ile Ala Ser Leu Asn Thr Arg Glu Leu
                85                  90                  95

Phe Glu Asn Val Phe Ile Gly Asn Glu Pro Thr Ala Lys Arg Ala Ile
            100                 105                 110

Ser Pro Val Leu Ile Ser Arg Leu Leu Glu Ala Asp Phe Ser Lys Asn
        115                 120                 125

Ser Arg Leu Asp Phe Ala Arg Asp Leu Phe Leu Ser Phe Tyr Leu
    130                 135                 140

Arg Gly Ile Pro Phe Val Asp Leu Val His Leu Arg Lys Thr Asp Val
145                 150                 155                 160

Gln Gly Asn Met Leu Val Tyr Phe Arg Gln Lys Thr Gly Gln Gln Leu
                165                 170                 175

Thr Val Ile Ile Glu Asn Cys Ala Lys Val Ile Leu Arg Lys Tyr Ala
            180                 185                 190

Ser Leu Cys Lys Glu Ser Val Tyr Leu Leu Pro Val Ile Ser Ala Ala
        195                 200                 205

Gly Glu Glu Gly His Lys Gln Tyr Arg Ser Ala Leu Arg Val Tyr Asn
    210                 215                 220

Lys Arg Leu Asn Gln Ile Ser Gly Ile Leu Lys Leu Lys Thr Pro Leu
225                 230                 235                 240

Thr Ser Tyr Val Ala Arg His Ser Trp Ala Thr Thr Ala Leu Gln Lys
                245                 250                 255

Gly Val Pro Val Ser Val Ile Ser Ala Gly Met Gly His Ala Ser Glu
            260                 265                 270

Lys Val Thr Tyr Ile Tyr Leu Ala Ser Phe Asp Asn Lys Thr Leu Ser
        275                 280                 285

Asn Ala Asn Lys Lys Val Ile Ala Ala Val Arg Phe Lys Lys Glu Glu
    290                 295                 300

Glu Glu
305
```

<210> SEQ ID NO 5
<211> LENGTH: 1958
<212> TYPE: DNA
<213> ORGANISM: Bacteroides fragilis

<400> SEQUENCE: 5

```
agtactgata actccggtga ctcccgccac tgtaaaagaa aatgccggag aagctcccca     60
gggacaagac gtaaacgcta cggtgaaaaa tgacacggtg ttcttcgaca aattgccggt    120
aaccgaactt attcctcca ttgtaggcga taaagacaaa gcggaagcca ttgtcaaagc    180
```

-continued

```
catcggtgac gtaaaataca aagtaggcta caagccggct ctcaacacag agaaggacag      240
catctacctt gctttcgatc cgaaaccgtt gacccttcaa ctgcctgcag ccgtagaagg      300
ccaggaagga cagactgtta ccgtaaccat ttcgtctccg gacaaaggca gctttgctta      360
caagaaaaat cagttgaagt tgaagctcag cgccgataaa gtggaactgg caggcgtagc      420
ggtacctgtt cctcagaccc tgttcgactt cggtatgacc aaaaagaagt gattgcctgt      480
tcaacacacg taacaagcag tagtcatagg gggtaaagcc tgtaaagaca ggctttatac      540
ccgcatgaaa aagtccgtgc tctcccccc ggagtgaaca cggactttct gttccttgaa       600
accattcaaa aaaaaagat tatttcacag cagccaatgc cttttcataa tccggctcct       660
gagtaatctc cggcacaagc tctgtataag ctactttccc gtctttccca atcaccacta      720
ccgcacgcgc cagcagtccg gccagcggtc cgtcagccat cctcacgcca tagctctcgt      780
cgaagtccga aaagcggaaa tccgacaacg gaatcacgtt ttcgataccc tctgtcgtgc      840
agaagcgtcc ctgcgcaaac ggcaagtctt tcgaaatggc caataccacg gtatccttca      900
ttccggctgc cattttattg aatttacgca ccgaagtggc gcacacaccg gtatccagac      960
tcgggaaaat attcagaaca atattcttac ctttcgatc ttttagtgcg aaagaagata      1020 aatcacttt caccagctcg aaatcgggag ccacctttcc aacctgtata aattcgccaa       1080 tcagcttac cggttgtcct tgaaatttg ttgttgccat aattgataac tctaagtttt        1140
atttactata ttctaaacaa tcggtgcaag aactttgttc acgatggaca taatctaaa       1200 aaataaaatt gatatgaaaa ctttattcga cgagatggaa cacgcagtca aaaactggtg      1260
gttatctctt attctgggta ttctgtacat catcgtggct ctctgtctgc tattcgcacc      1320
gggaagcagt tacattgccc tcagcgtcat cttcagcatt tcgatgctga taagtggtat      1380
catcgaaatc atcttctcca tcagtaaccg gcgaggcatc tcgtcctggg gatggtacct      1440
cgcaggcggt atcatcgatc tgatcttagg catctacctg gtagcctatc cgctgctcag      1500
catggaagtc ataccgttca tagtcgcctt ctggatgatg ttccgcggtt tctccgccac      1560
aggctattct atggacctga agcgttatgg cacccgtgag tggggatggt acatgggatt      1620
cggcatcctc gccatcattt gttcgctgat catcctgtgg cagccggccg taggtgccct      1680
ctacgttata tatatgctgg cattcacttt cctgatcatc ggattcttcc gtgtcatgtt      1740
gtccttcgaa ctgaaaagcc ttcataaacg atcaacggtg atgaacggta atgataaac       1800 attgaatgaa cccctattca ccacagatta cacagattaa cacagatatt ttaattaaac      1860
tctcagtaaa ataattatt aatctgtgag aatctgtgta atctgcggtg aattatgact       1920
cccctaaccg ttactaatac atcgttttca taaaccgg                              1958
```

<210> SEQ ID NO 6
<211> LENGTH: 2540
<212> TYPE: DNA
<213> ORGANISM: Bacteroides fragilis

<400> SEQUENCE: 6

```
ttttccgtac ttactctcaa ataagctatt accataattc atgttttaa atgattaata       60 caccacgaaa aaacggctat tcattcaaat acgggacact tttttacgtt ccttttttct      120
catgccactt gggtatttct gaaactttca ttcgtctata catttatgct attgattttt      180
tactaatttc cagcatattt tccaatctgt cactcaaaat cttttttatt ataaaccgtg      240
ttcttgaaca cactaaaaag aacaagaaaa tggaaataga aaaattcatt aaatctttag      300
caagaaaagc gaagttaggc gggcgttaca gcacagccaa tacctacctc tacactttgc      360
```

```
acagttttca gaagtttgcg ggaaaagcct cactgacttt tgaagagatc actcccgaga    420
gtatcaagga gtacgagcaa tacttaatcc tcaacgggaa acggtacaac acgatctcgc    480
tctacatgcg catgttgcgt tccatctgca atcaggcatc ggagcagaac atagcttcgc    540
tcaacacccg cgagctgttt gagaatgttt ttatcggcaa cgaacccact gccaagcgtg    600
ccatctcacc cgtcctcatt tcccgcctgc tcgaagcaga tttcagcaag aacagccggc    660
tcgattttgc ccgcgacctc ttcttgctaa gcttctacct gagggaatc  ccgtttgtcg    720
acctggtaca tctccgcaag accgatgtgc agggaaacat gctcgtttat ttccgccaga    780
aaacgggaca gcaacttacg gtaatcatag aaaactgcgc caaagtgatc ttgcgtaagt    840
atgcctcgct ttgcaaagaa tccgtctatc tgctgcccgt catcagcgca gccggagagg    900
aggggcacaa gcagtaccga agtgcattga gggtatacaa caaacgcctc aaccagatat    960
ccggaatact gaaattgaag actccgctga cctcttatgt ggcacgccac agttgggcga   1020
ccacggccct gcagaaaggg gttccggttt cagtgatcag tgcaggaatg gggcatgctt   1080
cagagaaggt gacatacatt tatctggcat cttttgataa caaaacgctc agtaacgcaa   1140
ataaaaaagt gattgccgcc gtgagattta agaaagagga ggaggagtga taatagctgt   1200
tctcttactt attaggtaat agaacagatt catttgtttt atcgctgcaa aaatagagat   1260
aataattgaa actccacaaa caaaatgata atttctttc  tataaaagtg gattataacc   1320
agttgaagta tcagtttgaa ataatttatt cacttaatag aaatattagt cataattcct   1380
gtttgatgta attactcaaa caggagttta caatttgcaa taatttgaca tcagaattat   1440
ataatccagc ccctgtttta tgtttagtta acctctaaaa gttatatttc atatcttttc   1500
gctattccgc attctattac ctaataagta agggatcact tgttctatt  acctaataag   1560
taagggaaca aattgcaatg cacacagcaa gatggtagtt attcaaacat taacgacaac   1620
tatcgcaaac atttctaaaa gtacagtatg aaacaggtat tgcggttcaa taaagtcatt   1680
aaaaggattg tattcaccgg agatctcatt ctcttgaatg gcacctttct gtccttgtac   1740
acccctattgg ggagcaaatt ttttgcagat ccattcattc actcacttcc ccaagtactg   1800
gtattgctca acttatgcta cctggttagc aacatgtctt caggtatcat attgcaccgc   1860
cgtgtagtac gtcccgagca aatcgtatgg cgtgccttac gcaacagtgc gggacacgcc   1920
ttgtttttt  cctgcgcgct cacctttgga aacttcggca tcctttccgc ccgcttttc    1980
ttactgttct acattgcgtt cactctgctg ttggtttgtt accggttatt gttccgcaag   2040
atcctgaagt cctatcgtaa gcatggaggc aactcccgca gcatcattct ggtgggaagc   2100
aatagcaata taatcgaact ctaccatcaa atgacggacg acgtcacttc cggattccgt   2160
gtcatcggct actttgacga ccagccaggc agccgcttcc ccgaaaaggt gaactatctg   2220
ggaaaacccg gtaagattgt ggaccgcctg aagcagggag gagtcgagca ggtttattgt   2280
tgcctgcctt cggcccgcag cgaagagatt ctccccatca tcgactattg cgaaaatcac   2340
ctgatacgct ttttcagtgt ccccaacgtg cgcagctatc tgaagcggcg catgtacttc   2400
gagctcctgg gcaacgtgcc cgtactctgc atccgccagg agccgctcag ttttgccgaa   2460
aaccgattca ggaagcgtgt gttcgacatc gctttctcgc tcttgtttct ttgcaccctc   2520
ttccccatta tctatgtcat                                               2540
```

<210> SEQ ID NO 7
<211> LENGTH: 19
<212> TYPE: DNA
<213> ORGANISM: Bacteroides fragilis

<400> SEQUENCE: 7
acgaacgttt tttgaaaca                                                    19

<210> SEQ ID NO 8
<211> LENGTH: 22
<212> TYPE: DNA
<213> ORGANISM: Bacteroides fragilis

<400> SEQUENCE: 8
tagacgatcg tctattgaaa ca                                                22

<210> SEQ ID NO 9
<211> LENGTH: 25
<212> TYPE: DNA
<213> ORGANISM: Bacteroides fragilis

<400> SEQUENCE: 9
ttaaacgaac gtctattgaa acact                                             25

<210> SEQ ID NO 10
<211> LENGTH: 20
<212> TYPE: DNA
<213> ORGANISM: Bacteroides fragilis

<400> SEQUENCE: 10
gttcaaatag acgaacgttt                                                   20

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 11
ccggatccag tactgataac tccggtgact cc                                     32

<210> SEQ ID NO 12
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 12
atccatggcc ggtttatgaa aacgatgtat ta                                     32

<210> SEQ ID NO 13
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 13
cgccatggtt ttccgtactt actctcaaat aagc                                   34

<210> SEQ ID NO 14
<211> LENGTH: 32
<212> TYPE: DNA

```
<213> ORGANISM: Artificial sequence
<220> FEATURE:
<223> OTHER INFORMATION: Synthetic oligonucleotide

<400> SEQUENCE: 14
ggggatccat gacatagata atggggaaga gg                                      32
```